(12) United States Patent
Dietrich et al.

(10) Patent No.: US 8,552,169 B2
(45) Date of Patent: Oct. 8, 2013

(54) TRANSCRIPTION FACTOR-BASED BIOSENSOR

(75) Inventors: Jeffrey A. Dietrich, San Francisco, CA (US); Jay D. Keasling, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 12/767,649

(22) Filed: Apr. 26, 2010

(65) Prior Publication Data

US 2011/0065105 A1 Mar. 17, 2011

Related U.S. Application Data

(60) Provisional application No. 61/172,678, filed on Apr. 24, 2009.

(51) Int. Cl.
*C07H 21/04* (2006.01)
*C12Q 1/00* (2006.01)

(52) U.S. Cl.
USPC .............................................. 536/24.1; 435/4

(58) Field of Classification Search
None
See application file for complete search history.

(56) References Cited

U.S. PATENT DOCUMENTS 4,551,433 A 11/1985 DeBoer

OTHER PUBLICATIONS

Sayavedra-Soto, Product and product-independent induction of butane oxidation in *Pseudomonas butanovora*, FEMS Microbiology Letters 250 (2005) 111-116.*
Guarente, L. (1983) Yeast promoters and lacZ fusions designed to study expression of cloned genes in yeast. Methods Enzymol. 101, 181-191.*
Buck et al., "The Bacterial Enhancer-Dependent σ54 (σN) Transcription Factor", Journal of Bacteriology, vol. 182, No. 15, Aug. 2000, p. 4129-4136.
Guzman et al., "Tight Regulation, Modulation, and High-Level Expression by Vectors Containing the Arabinose PBAD Promoter", Journal of Bacteriology, vol. 177, No. 14, Jul. 1995, p. 4121-4130.
Kurth et al., "Involvement of BmoR and BmoG in n-alkane metabolism in '*Pseudomonas butanovora*'", Microbiology (2008), 154, 139-147.
Lee et al., "A Propionate-Inducible Expression System for Enteric Bacteria", Applied and Environmental Microbiology, vol. 71, No. 11, Nov. 2005, p. 6856-6862.
Merrick et al., "In a class of its own—the RNA polymerase sigma factor σ54 (σN)", Molecular Microbiology (1993) 10(5), 903-909.
Sluis et al., "Molecular analysis of the soluble butane monooxygenase from '*Pseudomonas butanovora*'", Microbiology (2002), 148, 3617-3629.

* cited by examiner

*Primary Examiner* — Jim Ketter
*Assistant Examiner* — Reza Ghafoorian
(74) *Attorney, Agent, or Firm* — Robin C. Chiang; Lawrence Berkeley National Laboratory

(57) ABSTRACT

The present invention provides for a system comprising a BmoR transcription factor, a $\sigma^{54}$-RNA polymerase, and a pBMO promoter operatively linked to a reporter gene, wherein the pBMO promoter is capable of expression of the reporter gene with an activated form of the BmoR and the $\sigma^{54}$-RNA polymerase.

32 Claims, 6 Drawing Sheets

- Clarified Lysate
- Flow-through
- 50 mM imidazole
- 50 mM imidazole
- 100 mM imidazole
- 150 mM imidazole
- 500 mM imidazole elution

SEQUENCE LISTING

```
<160> NUMBER OF SEQ ID NOS: 17

<210> SEQ ID NO 1
<211> LENGTH: 497
<212> TYPE: PRT
<213> ORGANISM: Pseudomonas putida

<400> SEQUENCE: 1
```

Met Lys Pro Ser Leu Val Leu Lys Met Gly Gln Gln Leu Thr Met Thr
1               5                   10                  15

Pro Gln Leu Gln Gln Ala Ile Arg Leu Leu Gln Leu Ser Thr Leu Asp
                20                  25                  30

Leu Gln Gln Glu Ile Gln Glu Ala Leu Glu Ser Asn Pro Met Leu Glu
            35                  40                  45

Arg Gln Glu Asp Gly Glu Asp Phe Asp Asn Ser Asp Pro Met Ala Asp
        50                  55                  60

Asn Ala Glu Asn Lys Pro Ala Ala Glu Val Gln Asp Asn Ser Phe Gln
65                  70                  75                  80

-continued

```
Glu Ser Thr Val Ser Ala Asp Asn Leu Glu Asp Gly Glu Trp Ser Glu
                 85                  90                  95
Arg Ile Pro Asn Glu Leu Pro Val Asp Thr Ala Trp Glu Asp Ile Tyr
            100                 105                 110
Gln Thr Ser Ala Ser Ser Leu Pro Ser Asn Asp Asp Glu Trp Asp
            115                 120                 125
Phe Thr Thr Arg Thr Ser Ala Gly Glu Ser Leu Gln Ser His Leu Leu
        130                 135                 140
Trp Gln Leu Asn Leu Ala Pro Met Ser Asp Thr Asp Arg Leu Ile Ala
145                 150                 155                 160
Val Thr Leu Ile Asp Ser Ile Asn Gly Gln Gly Tyr Leu Glu Asp Thr
                165                 170                 175
Leu Glu Glu Ile Ser Ala Gly Phe Asp Pro Glu Leu Asp Ile Glu Leu
            180                 185                 190
Asp Glu Val Glu Ala Val Leu His Arg Ile Gln Gln Phe Glu Pro Ala
            195                 200                 205
Gly Val Gly Ala Arg Asn Leu Gly Glu Cys Leu Leu Leu Gln Leu Arg
        210                 215                 220
Gln Leu Pro Ala Thr Thr Pro Trp Met Thr Glu Ala Lys Arg Leu Val
225                 230                 235                 240
Thr Asp Phe Ile Asp Leu Leu Gly Ser Arg Asp Tyr Ser Gln Leu Met
                245                 250                 255
Arg Arg Met Lys Ile Lys Glu Asp Glu Leu Arg Gln Val Ile Glu Leu
            260                 265                 270
Val Gln Ser Leu Asn Pro Arg Pro Gly Ser Gln Ile Glu Ser Ser Glu
            275                 280                 285
Pro Glu Tyr Val Val Pro Asp Val Ile Val Arg Lys Asp Ser Asp Arg
        290                 295                 300
Trp Leu Val Glu Leu Asn Gln Glu Ala Ile Pro Arg Leu Arg Val Asn
305                 310                 315                 320
Pro Gln Tyr Ala Gly Phe Val Arg Arg Ala Asp Thr Ser Ala Asp Asn
                325                 330                 335
Thr Phe Met Arg Asn Gln Leu Gln Glu Ala Arg Trp Phe Ile Lys Ser
            340                 345                 350
Leu Gln Ser Arg Asn Glu Thr Leu Met Lys Val Ala Thr Arg Ile Val
            355                 360                 365
Glu His Gln Arg Gly Phe Leu Asp His Gly Asp Glu Ala Met Lys Pro
        370                 375                 380
Leu Val Leu His Asp Ile Ala Glu Ala Val Gly Met His Glu Ser Thr
385                 390                 395                 400
Ile Ser Arg Val Thr Thr Gln Lys Tyr Met His Thr Pro Arg Gly Ile
                405                 410                 415
Tyr Glu Leu Lys Tyr Phe Phe Ser Ser His Val Ser Thr Ser Glu Gly
            420                 425                 430
Gly Glu Cys Ser Ser Thr Ala Ile Arg Ala Ile Ile Lys Lys Leu Val
        435                 440                 445
Ala Ala Glu Asn Gln Lys Lys Pro Leu Ser Asp Ser Lys Ile Ala Gly
            450                 455                 460
Leu Leu Glu Ala Gln Gly Ile Gln Val Ala Arg Arg Thr Val Ala Lys
465                 470                 475                 480
Tyr Arg Glu Ser Leu Gly Ile Ala Pro Ser Ser Glu Arg Lys Arg Leu
                485                 490                 495
Met
```

<210> SEQ ID NO 2
<211> LENGTH: 497
<212> TYPE: PRT
<213> ORGANISM: Pseudomonas aeruginosa

<400> SEQUENCE: 2

Met Lys Pro Ser Leu Val Leu Lys Met Gly Gln Gln Leu Thr Met Thr
1               5                   10                  15

Pro Gln Leu Gln Gln Ala Ile Arg Leu Leu Gln Leu Ser Thr Leu Asp
            20                  25                  30

Leu Gln Gln Glu Ile Gln Glu Ala Leu Glu Ser Asn Pro Met Leu Glu
        35                  40                  45

Arg Gln Glu Asp Gly Asp Asp Phe Asp Asn Ser Asp Pro Leu Ala Asp
    50                  55                  60

Gly Ala Glu Gln Ala Ala Ser Ala Pro Gln Glu Ser Pro Leu Gln Glu
65                  70                  75                  80

Ser Ala Thr Pro Ser Val Glu Ser Leu Asp Asp Gln Trp Ser Glu
                85                  90                  95

Arg Ile Pro Ser Glu Leu Pro Val Asp Thr Ala Trp Glu Asp Ile Tyr
            100                 105                 110

Gln Thr Ser Ala Ser Ser Leu Pro Ser Asn Asp Asp Glu Trp Asp
        115                 120                 125

Phe Thr Ala Arg Thr Ser Ser Gly Glu Ser Leu His Ser Leu Leu
    130                 135                 140

Trp Gln Val Asn Leu Ala Pro Met Ser Asp Thr Asp Arg Met Ile Ala
145                 150                 155                 160

Val Thr Ile Ile Asp Ser Ile Asn Asn Asp Gly Tyr Leu Glu Ser
                165                 170                 175

Leu Glu Glu Ile Leu Ala Ala Ile Asp Pro Glu Leu Asp Val Gly Leu
            180                 185                 190

Asp Glu Val Glu Val Val Leu Arg Arg Ile Gln Leu Glu Pro Ala
        195                 200                 205

Gly Ile Gly Ala Arg Asn Leu Arg Glu Cys Leu Leu Leu Gln Leu Arg
    210                 215                 220

Gln Leu Pro Ser Thr Thr Pro Trp Leu Asn Glu Ala Leu Arg Leu Val
225                 230                 235                 240

Ser Asp Tyr Leu Asp Leu Leu Gly Gly Arg Asp Tyr Ser Gln Leu Met
                245                 250                 255

Arg Arg Met Lys Leu Lys Glu Asp Glu Leu Arg Gln Val Ile Glu Leu
            260                 265                 270

Ile Gln Cys Leu His Pro Arg Pro Gly Ser Gln Ile Glu Ser Ser Glu
        275                 280                 285

Ala Glu Tyr Ile Val Pro Asp Val Ile Val Arg Lys Asp Asn Glu Arg
    290                 295                 300

Trp Leu Val Glu Leu Asn Gln Glu Ala Met Pro Arg Leu Arg Val Asn
305                 310                 315                 320

Ala Thr Tyr Ala Gly Met Val Arg Arg Ala Asp Ser Ser Ala Asp Asn
                325                 330                 335

Thr Phe Met Arg Asn Gln Leu Gln Glu Ala Arg Trp Phe Ile Lys Thr
            340                 345                 350

Leu Gln Ser Arg Asn Glu Thr Leu Met Lys Val Ala Thr Gln Ile Val
        355                 360                 365

Glu His Gln Arg Gly Phe Leu Asp Tyr Gly Glu Ala Met Lys Pro
    370                 375                 380

```
Leu Val Leu His Asp Ile Ala Glu Ala Val Gly Met His Glu Ser Thr
385                 390                 395                 400

Ile Ser Arg Val Thr Thr Gln Lys Tyr Met His Thr Pro Arg Gly Ile
                405                 410                 415

Phe Glu Leu Lys Tyr Phe Phe Ser Ser His Val Ser Thr Ala Glu Gly
            420                 425                 430

Gly Glu Cys Ser Ser Thr Ala Ile Arg Ala Ile Ile Lys Lys Leu Val
        435                 440                 445

Ala Ala Glu Asn Ala Lys Lys Pro Leu Ser Asp Ser Lys Ile Ala Gly
    450                 455                 460

Leu Leu Glu Ala Gln Gly Ile Gln Val Ala Arg Arg Thr Val Ala Lys
465                 470                 475                 480

Tyr Arg Glu Ser Leu Gly Ile Ala Pro Ser Ser Glu Arg Lys Arg Leu
                485                 490                 495

Val

<210> SEQ ID NO 3
<211> LENGTH: 489
<212> TYPE: PRT
<213> ORGANISM: Vibrio fischeri

<400> SEQUENCE: 3

Met Lys Ala Ser Leu Gln Leu Lys Met Gly Gln Gln Leu Ala Met Thr
1               5                   10                  15

Pro Gln Leu Gln Gln Ala Ile Arg Leu Leu Gln Leu Ser Thr Leu Asp
                20                  25                  30

Leu Gln Gln Glu Ile Gln Glu Ala Leu Asp Ser Asn Pro Leu Leu Asp
            35                  40                  45

Val Glu Glu Ala Leu Ser Thr Pro Glu Thr Leu Thr Ser Pro Glu
    50                  55                  60

Pro Lys Ser Glu Lys Glu Thr Ala Ser Ala Glu Gln Glu Thr Pro Ile
65                  70                  75                  80

Thr Asp Ser Ser Asp Val Ile Glu Ser Asn Asn Ile Ser Glu Glu Leu
                85                  90                  95

Glu Met Asp Ala Ser Trp Asp Asp Val Tyr Ser Ala Asn Ser Gly Ser
            100                 105                 110

Thr Gly Leu Ala Ile Asp Asp Thr Pro Ile Tyr Gln Gly Glu Thr
        115                 120                 125

Thr Glu Ser Leu Gln Asp Tyr Leu Met Trp Gln Ala Asp Leu Thr Pro
    130                 135                 140

Phe Thr Asp Leu Asp Arg Thr Ile Ala Thr Thr Ile Ile Glu Ser Leu
145                 150                 155                 160

Asp Glu Tyr Gly Tyr Leu Thr Ser Ser Leu Asp Ile Leu Glu Ser
                165                 170                 175

Ile Gly Asp Glu Glu Val Glu Met Asp Glu Val Glu Ala Val Leu Lys
            180                 185                 190

Arg Ile Gln Gln Phe Asp Pro Leu Gly Val Ala Ser Arg Asp Leu Ala
        195                 200                 205

Glu Cys Leu Leu Leu Gln Leu Ala Thr Tyr Pro Ala Asn Thr Pro Trp
    210                 215                 220

Leu Pro Glu Thr Lys Leu Ile Leu Lys Asp His Ile Asn Leu Leu Gly
225                 230                 235                 240

Asn Arg Asp Tyr Arg Gln Leu Ala Lys Glu Thr Lys Leu Lys Glu Ser
                245                 250                 255

Asp Leu Lys Gln Val Met Met Leu Ile His Glu Leu Asp Pro Arg Pro
```

```
            260                 265                 270
Gly Asn Arg Val Ile Asp Thr Glu Thr Glu Tyr Val Ile Pro Asp Val
        275                 280                 285

Ser Val Phe Lys His Asn Gly Lys Trp Val Val Thr Ile Asn Pro Asp
    290                 295                 300

Ser Val Pro Arg Leu Lys Val Asn Ala Glu Tyr Ala Ala Leu Gly Lys
305                 310                 315                 320

Thr Met Gly Asn Thr Pro Asp Gly Gln Phe Ile Arg Thr Asn Leu Gln
                325                 330                 335

Glu Ala Lys Trp Leu Ile Lys Ser Leu Glu Ser Arg Asn Glu Thr Leu
            340                 345                 350

Leu Lys Val Ala Arg Cys Ile Val Glu His Gln Gln Asp Phe Phe Glu
        355                 360                 365

Tyr Gly Glu Glu Ala Met Lys Pro Met Val Leu Asn Asp Ile Ala Leu
    370                 375                 380

Asp Val Asp Met His Glu Ser Thr Ile Ser Arg Val Thr Thr Gln Lys
385                 390                 395                 400

Phe Met His Thr Pro Arg Gly Ile Phe Glu Leu Lys Tyr Phe Phe Ser
                405                 410                 415

Ser His Val Ser Thr Asp Asn Gly Gly Glu Cys Ser Ser Thr Ala Ile
            420                 425                 430

Arg Ala Leu Val Lys Lys Leu Val Ala Ala Glu Asn Gln Ala Lys Pro
        435                 440                 445

Leu Ser Asp Ser Lys Ile Ala Thr Leu Leu Ala Glu Gln Gly Ile Gln
    450                 455                 460

Val Ala Arg Arg Thr Ile Ala Lys Tyr Arg Glu Ser Leu Gly Ile Ala
465                 470                 475                 480

Pro Ser Asn Gln Arg Lys Arg Leu Leu
                485

<210> SEQ ID NO 4
<211> LENGTH: 669
<212> TYPE: PRT
<213> ORGANISM: Pseudomonas butanova

<400> SEQUENCE: 4

Met Ser Lys Met Gln Glu Phe Ala Arg Leu Glu Thr Val Ala Ser Met
1               5                   10                  15

Arg Arg Ala Val Trp Asp Gly Asn Glu Cys Gln Pro Gly Lys Val Ala
            20                  25                  30

Asp Val Val Leu Arg Ser Trp Thr Arg Cys Arg Ala Glu Gly Val Val
        35                  40                  45

Pro Asn Ala Arg Gln Glu Phe Asp Pro Ile Pro Arg Thr Ala Leu Asp
    50                  55                  60

Glu Thr Val Glu Ala Lys Arg Ala Leu Ile Leu Ala Ala Glu Pro Val
65                  70                  75                  80

Val Asp Ala Leu Met Glu Gln Met Asn Asp Ala Pro Arg Met Ile Ile
                85                  90                  95

Leu Asn Asp Glu Arg Gly Val Val Leu Leu Asn Gln Gly Asn Asp Thr
            100                 105                 110

Leu Leu Glu Asp Ala Arg Arg Ala Val Arg Val Gly Val Cys Trp
        115                 120                 125

Asp Glu His Ala Arg Gly Thr Asn Ala Met Gly Thr Ala Leu Ala Glu
    130                 135                 140

Arg Arg Pro Val Ala Ile His Gly Ala Glu His Tyr Leu Glu Ser Asn
```

-continued

```
            145                 150                 155                 160
        Thr Ile Phe Thr Cys Thr Ala Ala Pro Ile Tyr Asp Pro Phe Gly Glu
                        165                 170                 175
        Phe Thr Gly Ile Leu Asp Ile Ser Gly Tyr Ala Gly Asp Met Gly Pro
                        180                 185                 190
        Val Pro Ile Pro Phe Val Gln Met Ala Val Gln Phe Ile Glu Asn Gln
                        195                 200                 205
        Leu Phe Arg Gln Thr Phe Ala Asp Cys Ile Leu Leu His Phe His Val
                        210                 215                 220
        Arg Pro Asp Phe Val Gly Thr Met Arg Glu Gly Ile Ala Val Leu Ser
        225                 230                 235                 240
        Arg Glu Gly Thr Ile Val Ser Met Asn Arg Ala Gly Leu Lys Ile Ala
                        245                 250                 255
        Gly Leu Asn Leu Glu Ala Val Ala Asp His Arg Phe Asp Ser Val Phe
                        260                 265                 270
        Asp Leu Asn Phe Gly Ala Phe Leu Asp His Val Arg Gln Ser Ala Phe
                        275                 280                 285
        Gly Leu Val Arg Val Ser Leu Tyr Gly Gly Val Gln Val Tyr Ala Arg
                        290                 295                 300
        Val Glu Pro Gly Leu Arg Val Pro Arg Pro Ala Ala His Ala Arg
        305                 310                 315                 320
        Pro Pro Arg Pro Ala Pro Arg Pro Leu Asp Ser Leu Asp Thr Gly Asp
                        325                 330                 335
        Ala Ala Val Arg Leu Ala Ile Asp Arg Ala Arg Arg Ala Ile Gly Arg
                        340                 345                 350
        Asn Leu Ser Ile Leu Ile Gln Gly Glu Thr Gly Ala Gly Lys Glu Val
                        355                 360                 365
        Phe Ala Lys His Leu His Ala Glu Ser Pro Arg Ser Lys Gly Pro Phe
                        370                 375                 380
        Val Ala Val Asn Cys Ala Ala Ile Pro Glu Gly Leu Ile Glu Ser Glu
        385                 390                 395                 400
        Leu Phe Gly Tyr Glu Glu Gly Ala Phe Thr Gly Gly Arg Arg Lys Gly
                        405                 410                 415
        Asn Ile Gly Lys Val Ala Gln Ala His Gly Gly Thr Leu Phe Leu Asp
                        420                 425                 430
        Glu Ile Gly Asp Met Ala Pro Gly Leu Gln Thr Arg Leu Leu Arg Val
                        435                 440                 445
        Leu Gln Asp Arg Ala Val Met Pro Leu Gly Gly Arg Glu Pro Met Pro
        450                 455                 460
        Val Asp Ile Ala Leu Val Cys Ala Thr His Arg Asn Leu Arg Ser Leu
        465                 470                 475                 480
        Ile Ala Gln Gly Gln Phe Arg Glu Asp Leu Tyr Tyr Arg Leu Asn Gly
                        485                 490                 495
        Leu Ala Ile Ser Leu Pro Pro Leu Arg Gln Arg Ser Asp Leu Ala Ala
                        500                 505                 510
        Leu Val Asn His Ile Leu Phe Gln Cys Cys Gly Gly Glu Pro His Tyr
                        515                 520                 525
        Ser Val Ser Pro Glu Val Met Thr Leu Phe Lys Arg His Ala Trp Pro
                        530                 535                 540
        Gly Asn Leu Arg Gln Leu His Asn Val Leu Asp Ala Ala Leu Ala Met
        545                 550                 555                 560
        Leu Asp Asp Gly His Val Ile Glu Pro His His Leu Pro Glu Asp Phe
                        565                 570                 575
```

```
Val Met Glu Val Asp Ser Gly Leu Arg Pro Ile Glu Glu Asp Gly Ser
            580                 585                 590

Thr Ala Ala His Arg Ala Arg Gln Pro Ala Ser Gly Ser Gly Pro Ala
        595                 600                 605

Lys Lys Leu Gln Asp Leu Ala Leu Asp Ala Ile Glu Gln Ala Ile Glu
610                 615                 620

Gln Asn Glu Gly Asn Ile Ser Val Ala Ala Arg Gln Leu Gly Val Ser
625                 630                 635                 640

Arg Thr Thr Ile Tyr Arg Lys Leu Arg Gln Leu Ser Pro Thr Gly Cys
                645                 650                 655

His Arg Pro Ala His Trp Ser Gln Ser Arg Ile Gly Thr
            660                 665

<210> SEQ ID NO 5
<211> LENGTH: 23
<212> TYPE: DNA
<213> ORGANISM: Escherichia coli
<220> FEATURE:
<221> NAME/KEY: misc_feature
<222> LOCATION: (1)..(1)
<223> OTHER INFORMATION: m is c, or a
<220> FEATURE:
<221> NAME/KEY: misc_feature
<222> LOCATION: (2)..(2)
<223> OTHER INFORMATION: r is a, or g
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(12)
<223> OTHER INFORMATION: r is a, or g
<220> FEATURE:
<221> NAME/KEY: misc_feature
<222> LOCATION: (13)..(16)
<223> OTHER INFORMATION: n is a, c, g, or t
<220> FEATURE:
<221> NAME/KEY: misc_feature
<222> LOCATION: (21)..(21)
<223> OTHER INFORMATION: w is a, or t
<220> FEATURE:
<221> NAME/KEY: misc_feature
<222> LOCATION: (22)..(23)
<223> OTHER INFORMATION: n is a, c, g, or t

<400> SEQUENCE: 5
mrnnntggca crnnnnttgc wnn                                         23

<210> SEQ ID NO 6
<211> LENGTH: 24
<212> TYPE: DNA
<213> ORGANISM: Escherichia coli
<220> FEATURE:
<221> NAME/KEY: misc_feature
<222> LOCATION: (1)..(1)
<223> OTHER INFORMATION: m is c, or a
<220> FEATURE:
<221> NAME/KEY: misc_feature
<222> LOCATION: (2)..(2)
<223> OTHER INFORMATION: r is a, or g
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(12)
<223> OTHER INFORMATION: r is a, or g
<220> FEATURE:
<221> NAME/KEY: misc_feature
<222> LOCATION: (13)..(17)
```

-continued

```
<223> OTHER INFORMATION: n is a, c, g, or t
<220> FEATURE:
<221> NAME/KEY: misc_feature
<222> LOCATION: (22)..(22)
<223> OTHER INFORMATION: w is a, or t
<220> FEATURE:
<221> NAME/KEY: misc_feature
<222> LOCATION: (23)..(24)
<223> OTHER INFORMATION: n is a, c, g, or t

<400> SEQUENCE: 6
mrnnntggca crnnnnnttg cwnn                                          24

<210> SEQ ID NO 7
<211> LENGTH: 23
<212> TYPE: DNA
<213> ORGANISM: Escherichia coli
<220> FEATURE:
<221> NAME/KEY: misc_feature
<222> LOCATION: (1)..(1)
<223> OTHER INFORMATION: m is a, or c
<220> FEATURE:
<221> NAME/KEY: misc_feature
<222> LOCATION: (2)..(2)
<223> OTHER INFORMATION: r is a, or g
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (4)..(4)
<223> OTHER INFORMATION: r is a, or g
<220> FEATURE:
<221> NAME/KEY: misc_feature
<222> LOCATION: (5)..(5)
<223> OTHER INFORMATION: y is c, or t
<220> FEATURE:
<221> NAME/KEY: misc_feature
<222> LOCATION: (13)..(16)
<223> OTHER INFORMATION: n is a, c, g, or t
<220> FEATURE:
<221> NAME/KEY: misc_feature
<222> LOCATION: (21)..(21)
<223> OTHER INFORMATION: w is a, or t
<220> FEATURE:
<221> NAME/KEY: misc_feature
<222> LOCATION: (22)..(23)
<223> OTHER INFORMATION: n is a, c, g, or t

<400> SEQUENCE: 7
mrnrytggca cgnnnnttgc wnn                                           23

<210> SEQ ID NO 8
<211> LENGTH: 24
<212> TYPE: DNA
<213> ORGANISM: Escherichia coli
<220> FEATURE:
<221> NAME/KEY: misc_feature
<222> LOCATION: (1)..(1)
<223> OTHER INFORMATION: m is a, or c
<220> FEATURE:
<221> NAME/KEY: misc_feature
<222> LOCATION: (2)..(2)
<223> OTHER INFORMATION: r is a, or g
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (4)..(4)
<223> OTHER INFORMATION: r is a, or g
<220> FEATURE:
<221> NAME/KEY: misc_feature
<222> LOCATION: (5)..(5)
```

<223> OTHER INFORMATION: y is c, or t
<220> FEATURE:
<221> NAME/KEY: misc_feature
<222> LOCATION: (13)..(17)
<223> OTHER INFORMATION: n is a, c, g, or t
<220> FEATURE:
<221> NAME/KEY: misc_feature
<222> LOCATION: (22)..(22)
<223> OTHER INFORMATION: w is a, or t
<220> FEATURE:
<221> NAME/KEY: misc_feature
<222> LOCATION: (23)..(24)
<223> OTHER INFORMATION: n is a, c, g, or t

<400> SEQUENCE: 8
mrnrytggca cgnnnnnttg cwnn                                          24

<210> SEQ ID NO 9
<211> LENGTH: 26
<212> TYPE: DNA
<213> ORGANISM: Escherichia coli
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (14)..(17)
<223> OTHER INFORMATION: n is a, c, g, or t

<400> SEQUENCE: 9
aannntggca cagnnnnttg catatt                                        26

<210> SEQ ID NO 10
<211> LENGTH: 24
<212> TYPE: DNA
<213> ORGANISM: Escherichia coli

<400> SEQUENCE: 10
catgctggca cgacacttgc tgaa                                          24

<210> SEQ ID NO 11
<211> LENGTH: 360
<212> TYPE: DNA
<213> ORGANISM: Pseudomonas butanova
<220> FEATURE:
<221> NAME/KEY: misc_feature
<222> LOCATION: (327)..(327)
<223> OTHER INFORMATION: m is c, or a
<220> FEATURE:
<221> NAME/KEY: misc_feature
<222> LOCATION: (328)..(328)
<223> OTHER INFORMATION: r is a, or g
<220> FEATURE:
<221> NAME/KEY: misc_feature
<222> LOCATION: (329)..(331)
<223> OTHER INFORMATION: n is a, c, g, or t
<220> FEATURE:
<221> NAME/KEY: misc_feature
<222> LOCATION: (338)..(338)
<223> OTHER INFORMATION: r is a, or g
<220> FEATURE:
<221> NAME/KEY: misc_feature
<222> LOCATION: (339)..(342)
<223> OTHER INFORMATION: n is a, c, g, or t
<220> FEATURE:
<221> NAME/KEY: misc_feature
<222> LOCATION: (347)..(347)
<223> OTHER INFORMATION: w is a, or t
<220> FEATURE:
<221> NAME/KEY: misc_feature
<222> LOCATION: (348)..(349)
<223> OTHER INFORMATION: n is a, c, g, or t

<400> SEQUENCE: 11

```
ccacagatag taggtgctgc ggctgctcat gctcctgtcg cggtagcgcg ctgttacgcg    60
accgcccccg gacctcggcg gacagcgcgg aagattggaa acagcccgag cgtgcgtgcc   120
tcgggctgca tccttgccac acccaaccgg attcgtcgga ccgctcgaca ttcgcgttcg   180
ctcccgcggc gccgcgggtg taccgttgcg ttacagatgt acccttcttt aacgtgtaac   240
acacgcctgg agcggccaag agcccgcac cttgcggcgc gtcttcccca ggggcccacc    300
ggttgcggcc ttttgctgcg accgtcmrnn ntggcacrnn nnttgcwnna agcgttagag   360
```

<210> SEQ ID NO 12
<211> LENGTH: 361
<212> TYPE: DNA
<213> ORGANISM: Pseudomonas butanova
<220> FEATURE:
<221> NAME/KEY: misc_feature
<222> LOCATION: (327)..(327)
<223> OTHER INFORMATION: m is c, or a
<220> FEATURE:
<221> NAME/KEY: misc_feature
<222> LOCATION: (328)..(328)
<223> OTHER INFORMATION: r is a, or g
<220> FEATURE:
<221> NAME/KEY: misc_feature
<222> LOCATION: (329)..(331)
<223> OTHER INFORMATION: n is a, c, g, or t
<220> FEATURE:
<221> NAME/KEY: misc_feature
<222> LOCATION: (338)..(338)
<223> OTHER INFORMATION: r is a, or g
<220> FEATURE:
<221> NAME/KEY: misc_feature
<222> LOCATION: (339)..(343)
<223> OTHER INFORMATION: n is a, c, g, or t
<220> FEATURE:
<221> NAME/KEY: misc_feature
<222> LOCATION: (348)..(348)
<223> OTHER INFORMATION: w is a, or t
<220> FEATURE:
<221> NAME/KEY: misc_feature
<222> LOCATION: (349)..(350)
<223> OTHER INFORMATION: n is a, c, g, or t

<400> SEQUENCE: 12

```
ccacagatag taggtgctgc ggctgctcat gctcctgtcg cggtagcgcg ctgttacgcg    60
accgcccccg gacctcggcg gacagcgcgg aagattggaa acagcccgag cgtgcgtgcc   120
tcgggctgca tccttgccac acccaaccgg attcgtcgga ccgctcgaca ttcgcgttcg   180
ctcccgcggc gccgcgggtg taccgttgcg ttacagatgt acccttcttt aacgtgtaac   240
acacgcctgg agcggccaag agcccgcac cttgcggcgc gtcttcccca ggggcccacc    300
ggttgcggcc ttttgctgcg accgtcmrnn ntggcacrnn nnttgcwnn aagcgttaga    360
g                                                                   361
```

<210> SEQ ID NO 13
<211> LENGTH: 360
<212> TYPE: DNA
<213> ORGANISM: Pseudomonas butanova
<220> FEATURE:
<221> NAME/KEY: misc_feature
<222> LOCATION: (327)..(327)
<223> OTHER INFORMATION: m is c, or a
<220> FEATURE:
<221> NAME/KEY: misc_feature
<222> LOCATION: (328)..(328)
<223> OTHER INFORMATION: r is a, or g
<220> FEATURE:
<221> NAME/KEY: misc_feature
<222> LOCATION: (329)..(329)

```
<223> OTHER INFORMATION: n is a, c, g, or t
<220> FEATURE:
<221> NAME/KEY: misc_feature
<222> LOCATION: (330)..(330)
<223> OTHER INFORMATION: r is a, or g
<220> FEATURE:
<221> NAME/KEY: misc_feature
<222> LOCATION: (331)..(331)
<223> OTHER INFORMATION: y is c, or t
<220> FEATURE:
<221> NAME/KEY: misc_feature
<222> LOCATION: (339)..(342)
<223> OTHER INFORMATION: n is a, c, g, or t
<220> FEATURE:
<221> NAME/KEY: misc_feature
<222> LOCATION: (347)..(347)
<223> OTHER INFORMATION: w is a, or t
<220> FEATURE:
<221> NAME/KEY: misc_feature
<222> LOCATION: (348)..(349)
<223> OTHER INFORMATION: n is a, c, g, or t

<400> SEQUENCE: 13
ccacagatag taggtgctgc ggctgctcat gctcctgtcg cggtagcgcg ctgttacgcg      60 accgccccg gacctcggcg gacagcgcgg aagattggaa acagcccgag cgtgcgtgcc     120
tcgggctgca tccttgccac acccaaccgg attcgtcgga ccgctcgaca ttcgcgttcg    180
ctcccgcggc gccgcgggtg taccgttgcg ttacagatgt acccttcttt aacgtgtaac    240
acacgcctgg agcggccaag agccccgcac cttgcggcgc gtcttcccca ggggcccacc    300
ggttgcggcc ttttgctgcg accgtcmrnr ytggcacgnn nnttgcwnna agcgttagag    360

<210> SEQ ID NO 14
<211> LENGTH: 361
<212> TYPE: DNA
<213> ORGANISM: Pseudomonas butanova
<220> FEATURE:
<221> NAME/KEY: misc_feature
<222> LOCATION: (327)..(327)
<223> OTHER INFORMATION: m is c, or a
<220> FEATURE:
<221> NAME/KEY: misc_feature
<222> LOCATION: (328)..(328)
<223> OTHER INFORMATION: r is a, or g
<220> FEATURE:
<221> NAME/KEY: misc_feature
<222> LOCATION: (329)..(329)
<223> OTHER INFORMATION: n is a, c, g, or t
<220> FEATURE:
<221> NAME/KEY: misc_feature
<222> LOCATION: (330)..(330)
<223> OTHER INFORMATION: r is a, or g
<220> FEATURE:
<221> NAME/KEY: misc_feature
<222> LOCATION: (331)..(331)
<223> OTHER INFORMATION: y is c, or t
<220> FEATURE:
<221> NAME/KEY: misc_feature
<222> LOCATION: (339)..(343)
<223> OTHER INFORMATION: n is a, c, g, or t
<220> FEATURE:
<221> NAME/KEY: misc_feature
<222> LOCATION: (348)..(348)
<223> OTHER INFORMATION: w is a, or t
<220> FEATURE:
<221> NAME/KEY: misc_feature
<222> LOCATION: (349)..(350)
<223> OTHER INFORMATION: n is a, c, g, or t

<400> SEQUENCE: 14
ccacagatag taggtgctgc ggctgctcat gctcctgtcg cggtagcgcg ctgttacgcg      60 accgccccg gacctcggcg gacagcgcgg aagattggaa acagcccgag cgtgcgtgcc     120
```

-continued

```
tcgggctgca tccttgccac acccaaccgg attcgtcgga ccgctcgaca ttcgcgttcg    180
ctcccgcggc gccgcgggtg taccgttgcg ttacagatgt acccttcttt aacgtgtaac    240
acacgcctgg agcggccaag agccccgcac cttgcggcgc gtcttcccca ggggcccacc    300
ggttgcggcc ttttgctgcg accgtcmrnr ytggcacgnn nnnttgcwnn aagcgttaga    360
g                                                                   361
```

<210> SEQ ID NO 15
<211> LENGTH: 363
<212> TYPE: DNA
<213> ORGANISM: Pseudomonas butanova
<220> FEATURE:
<221> NAME/KEY: misc_feature
<222> LOCATION: (329)..(331)
<223> OTHER INFORMATION: n is a, c, g, or t
<220> FEATURE:
<221> NAME/KEY: misc_feature
<222> LOCATION: (340)..(343)
<223> OTHER INFORMATION: n is a, c, g, or t

<400> SEQUENCE: 15

```
ccacagatag taggtgctgc ggctgctcat gctcctgtcg cggtagcgcg ctgttacgcg     60 accgccccg gacctcggcg gacagcgcgg aagattggaa acagcccgag cgtgcgtgcc    120
tcgggctgca tccttgccac acccaaccgg attcgtcgga ccgctcgaca ttcgcgttcg    180
ctcccgcggc gccgcgggtg taccgttgcg ttacagatgt acccttcttt aacgtgtaac    240
acacgcctgg agcggccaag agccccgcac cttgcggcgc gtcttcccca ggggcccacc    300
ggttgcggcc ttttgctgcg accgtcaann ntggcacagn nnnttgcata ttaagcgtta    360
gag                                                                 363
```

<210> SEQ ID NO 16
<211> LENGTH: 360
<212> TYPE: DNA
<213> ORGANISM: Pseudomonas butanova

<400> SEQUENCE: 16

```
ccacagatag taggtgctgc ggctgctcat gctcctgtcg cggtagcgcg ctgttacgcg     60 accgccccg gacctcggcg gacagcgcgg aagattggaa acagcccgag cgtgcgtgcc    120
tcgggctgca tccttgccac acccaaccgg attcgtcgga ccgctcgaca ttcgcgttcg    180
ctcccgcggc gccgcgggtg taccgttgcg ttacagatgt acccttcttt aacgtgtaac    240
acacgcctgg agcggccaag agccccgcac cttgcggcgc gtcttcccca ggggcccacc    300
ggttgcggcc ttttgctgcg accgtccatg ctggcacgac acttgctgaa agcgttagag    360
```

<210> SEQ ID NO 17
<211> LENGTH: 477
<212> TYPE: PRT
<213> ORGANISM: Escherichia coli

<400> SEQUENCE: 17

Met Lys Gln Gly Leu Gln Leu Arg Leu Ser Gln Gln Leu Ala Met Thr
1               5                   10                  15

Pro Gln Leu Gln Gln Ala Ile Arg Leu Leu Gln Leu Ser Thr Leu Glu
                20                  25                  30

Leu Gln Gln Glu Leu Gln Gln Ala Leu Glu Ser Asn Pro Leu Leu Glu
            35                  40                  45

Gln Ile Asp Thr His Glu Glu Ile Asp Thr Arg Glu Thr Gln Asp Ser
        50                  55                  60

-continued

Glu Thr Leu Asp Thr Ala Asp Ala Leu Glu Gln Lys Glu Met Pro Glu
65                  70                  75                  80

Glu Leu Pro Leu Asp Ala Ser Trp Asp Thr Ile Tyr Thr Ala Gly Thr
            85                  90                  95

Pro Ser Gly Thr Ser Gly Asp Tyr Ile Asp Asp Glu Leu Pro Val Tyr
            100                 105                 110

Gln Gly Glu Thr Thr Gln Thr Leu Gln Asp Tyr Leu Met Trp Gln Val
        115                 120                 125

Glu Leu Thr Pro Phe Ser Asp Thr Asp Arg Ala Ile Ala Thr Ser Ile
    130                 135                 140

Val Asp Ala Val Asp Glu Thr Gly Tyr Leu Thr Val Pro Leu Glu Asp
145                 150                 155                 160

Ile Leu Glu Ser Ile Gly Asp Glu Glu Ile Asp Ile Asp Glu Val Glu
                165                 170                 175

Ala Val Leu Lys Arg Ile Gln Arg Phe Asp Pro Val Gly Val Ala Ala
            180                 185                 190

Lys Asp Leu Arg Asp Cys Leu Leu Ile Gln Leu Ser Gln Phe Asp Lys
        195                 200                 205

Thr Thr Pro Trp Leu Glu Glu Ala Arg Leu Ile Ile Ser Asp His Leu
    210                 215                 220

Asp Leu Leu Ala Asn His Asp Phe Arg Thr Leu Met Arg Val Thr Arg
225                 230                 235                 240

Leu Lys Glu Asp Val Leu Lys Glu Ala Val Asn Leu Ile Gln Ser Leu
                245                 250                 255

Asp Pro Arg Pro Gly Gln Ser Ile Gln Thr Gly Glu Pro Glu Tyr Val
            260                 265                 270

Ile Pro Asp Val Leu Val Arg Lys His Asn Gly His Trp Thr Val Glu
        275                 280                 285

Leu Asn Ser Asp Ser Ile Pro Arg Leu Gln Ile Asn Gln His Tyr Ala
    290                 295                 300

Ser Met Cys Asn Asn Ala Arg Asn Asp Gly Asp Ser Gln Phe Ile Arg
305                 310                 315                 320

Ser Asn Leu Gln Asp Ala Lys Trp Leu Ile Lys Ser Leu Glu Ser Arg
                325                 330                 335

Asn Asp Thr Leu Leu Arg Val Ser Arg Cys Ile Val Glu Gln Gln Gln
            340                 345                 350

Ala Phe Phe Glu Gln Gly Glu Glu Tyr Met Lys Pro Met Val Leu Ala
        355                 360                 365

Asp Ile Ala Gln Ala Val Glu Met His Glu Ser Thr Ile Ser Arg Val
    370                 375                 380

Thr Thr Gln Lys Tyr Leu His Ser Pro Arg Gly Ile Phe Glu Leu Lys
385                 390                 395                 400

Tyr Phe Phe Ser Ser His Val Asn Thr Glu Gly Gly Glu Ala Ser
                405                 410                 415

Ser Thr Ala Ile Arg Ala Leu Val Lys Lys Leu Ile Ala Ala Glu Asn
            420                 425                 430

Pro Ala Lys Pro Leu Ser Asp Ser Lys Leu Thr Ser Leu Leu Ser Glu
        435                 440                 445

Gln Gly Ile Met Val Ala Arg Arg Thr Val Ala Lys Tyr Arg Glu Ser
    450                 455                 460

Leu Ser Ile Pro Pro Ser Asn Gln Arg Lys Gln Leu Val
465                 470                 475

TRANSCRIPTION FACTOR-BASED BIOSENSOR

RELATED PATENT APPLICATIONS

The application claims priority to U.S. Provisional Patent Application Ser. No. 61/172,678, filed Apr. 24, 2009, which is herein incorporated by reference in its entirety.

STATEMENT OF GOVERNMENTAL SUPPORT

The invention described and claimed herein was made in part utilizing funds supplied by the U.S. Department of Energy under Contract No. DE-AC02-05CH11231 and NIH Grant No. GM008352. The government has certain rights in this invention.

FIELD OF THE INVENTION

This invention relates generally to a transcription factor-based biosensor.

BACKGROUND OF THE INVENTION

In vivo biosensors for small molecules remain a valuable means through which one can design regulatory networks, build screens/selections, and quantify in vivo concentrations of metabolites of interest following system perturbations. Transcription activator and repressor proteins—proteins that modulate the activity of the RNA polymerase on a given promoter—serve as perhaps the most straight forward and controllable option for an in vivo biosensor. Further, transcription repressor/activator proteins are numerous in nature and there exist a wide range of low molecular weight ligands to which they respond. The value of an in vivo biosensor is intrinsically founded upon its transcription profile. An ideal in vivo biosensor would possess little-to-no basal level of expression in the absence of an input signal and the output signal would be linear over a large dynamic range.

Putatively, $\sigma^{54}$-dependent promoters and their associated activator proteins are ideally suited for use as in vivo biosensors. The sigma subunits of RNA polymerase specifically bind to DNA sequence elements and are responsible for differential gene expression. The primary, and most well understood, sigma factor is $\sigma^{70}$. $\sigma^{70}$ associates with the core RNA polymerase (E) to transcribe housekeeping genes. The complex E-$\sigma^{70}$ alone can be sufficient to catalyze the open promoter complex and allow RNA transcription. While activity can be controlled by various repressor proteins, leaky expression persists.

Absolute control, however, is accomplished through the use the much less common complex E-$\sigma^{54}$. While most bacteria contain several alternative $\sigma$ factors of the $\sigma^{70}$ class, usually only one $\sigma^{54}$ form exists. A $\sigma^{54}$-governed promoter is unique in that hydrolysis of the promoter DNA by an activator protein is an absolute requisite for transcription, imparting an intrinsically very low level of basal expression. ATP hydrolysis by activator proteins can be triggered by phosphorylation, binding of low molecular weight ligands, or protein-protein interaction. Further, without the need for a repressor protein, transcription levels can be tightly controlled over a large dynamic range. Lastly, the $\sigma^{54}$-based transcription system is a dedicated transcription system with little cross-talk; there exist close to 100 $\sigma^{54}$ molecules of in E. coli (compared to 700 of $\sigma^{70}$), while there are only 20 $\sigma^{54}$-governed promoters.

Use of $\sigma^{54}$-dependent promoters and their cognate activator proteins as biosensors in E. coli has been limited to date. Most of the 20 native E. coli $\sigma^{54}$-dependent promoters are induced in response to nitrogen limitation, potentially minimizing their use in biotechnology applications; however, prpBCDE promoters from Salmonella enteric serovar Typhimurium and E. coli have been explored by Lee, et al. as a propionate-inducible expression system (Lee, S. K., Keasling, J. D. A Propionate-Inducible Expression System for Enteric Bacteria. *Appl. Environ. Microbiol.* 71, 6856-6862 (2005)).

SUMMARY OF THE INVENTION

The present invention provides for a system comprising a BmoR transcription factor, a $\sigma^{54}$-RNA polymerase, and a pBMO promoter operatively linked to a reporter gene, wherein the pBMO promoter is capable of expression of the reporter gene with an activated form of the BmoR and the $\sigma^{54}$-RNA polymerase.

The present invention provides for a system comprising a first nucleic acid encoding a BmoR, and a second nucleic acid encoding a pBMO promoter operatively linked to a reporter gene, wherein the system is capable of expressing a $\sigma^{54}$-RNA polymerase and the pBMO promoter is capable of expression of the reporter gene.

The present invention provides for a modified host cell comprising a first nucleic acid encoding a BmoR, and a second nucleic acid encoding a pBMO promoter operatively linked to a reporter gene, wherein the modified host cell is capable of expressing a $\sigma^{54}$-RNA polymerase.

The present invention provides for an isolated or purified or recombinant BmoR. In some embodiments, the BmoR is bound to a DNA.

The present invention provides for a method for sensing a $C_2$-$C_8$ alcohol, aldehyde, or mixture thereof, comprising: (a) providing a modified host cell of the present invention, and (b) detecting the expression of the reporter gene.

In some embodiments of the invention, the (b) detecting step comprises detecting the gene product of the reporter gene. In some embodiments of the invention, the gene product of the reporter gene increases or decreases the doubling time of the modified host cell. In some embodiments of the invention, the gene product of the reporter gene causes the modified host cell to become resistant or sensitive to a compound.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION

Figure 1:
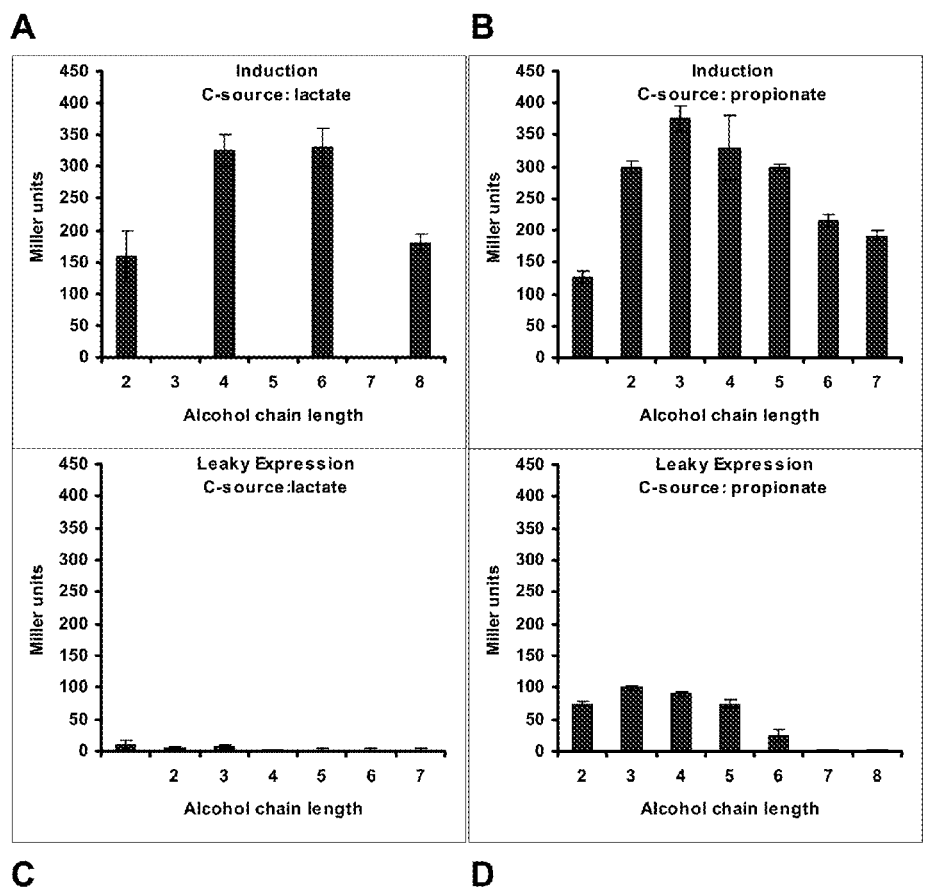
FIG. 1 shows the induction of β-galactosidase activity in a *P. butanova* lacZ reporter strain (X::lacZ) in which the bmo promoter controls the expression of a lacZ reporter cassette (Panels A and B), and in a mutant R8-X::lacZ reporter strain in which bmoR is insertionally inactivated (Panels C and D). (Panels A and C) Induction of β-galactosidase in X::lacZ (Panel A) and in mutant R8-X::lacZ (Panel C) in response to alcohols ($C_2$-$C_8$) following growth on lactate. (Panels B and D) Induction of β-galactosidase in X::lacZ (Panel B) and in mutant R8-X::lacZ (Panel D) in response to alcohols ($C_2$-$C_8$) following growth on propionate. (See Kurth, E. G., Doughty, D. M., Bottomley, P. J., Arp, D. J. & Sayavedra-Soto, L. A. Involvement of BmoR and BmoG in n-alkane metabolism in '*Pseudomonas butanovora*'. *Microbiology* 154, 139-147 (2008).)
Figure 2:
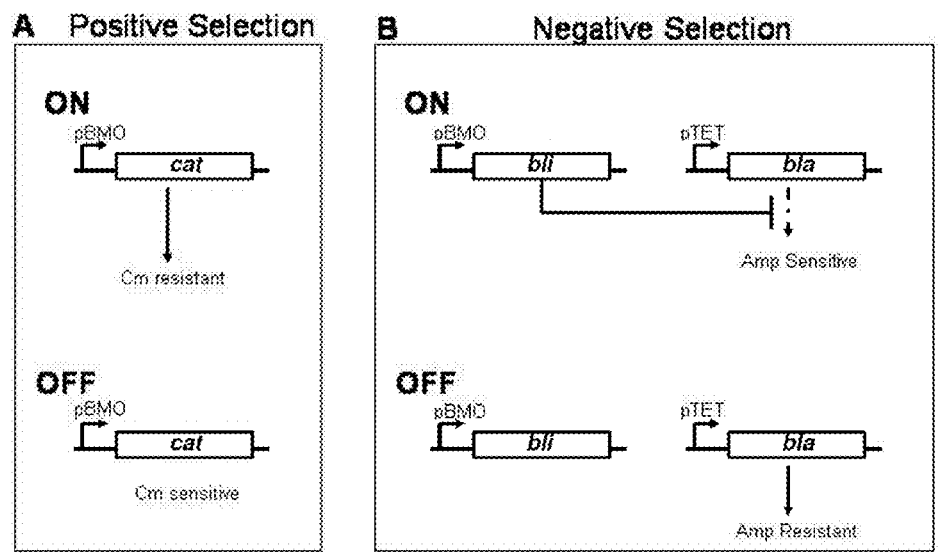
FIG. 2 shows an example of a positive selection (Panel A) and a negative selection (Panel B) constructs.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a carboxylic acid" includes a plurality of such carboxylic acids, and so forth.

In this specification and in the claims that follow, reference will be made to a number of terms that shall be defined to have the following meanings:

The terms "expression vector" or "vector" refer to a compound and/or composition that can be introduced into a host cell by any suitable method, including but not limited to transduction, transformation, transfection, infection, electroporation, conjugation, and the like; thereby causing the cell to express nucleic acids and/or proteins other than those native to the cell, or in a manner not native to the cell. An "expression vector" contains a sequence of nucleic acids (ordinarily RNA or DNA) to be expressed by the host cell. Optionally, the expression vector also comprises materials to aid in achieving entry of the nucleic acid into the host cell, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host cell and replicated therein. Particular expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The term "isolated" refers to material that is substantially or essentially free of components that normally accompany it in its native state.

As used herein, the terms "nucleic acid", "nucleotide" and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing normucleotidic backbones, provided that the polymers contain nucleobases in a configuration that allows for base pairing and base stacking, as found in DNA and RNA.

The term "operably linked" refers to a functional linkage between a nucleic acid expression control sequence (such as a promoter) and a second nucleic acid sequence, wherein the expression control sequence directs transcription of the nucleic acid corresponding to the second sequence.

These and other objects, advantages, and features of the invention will become apparent to those persons skilled in the art upon reading the details of the invention as more fully described below.

The present invention provides for a method for evolving and screening/selecting microorganisms producing an intracellular metabolite of interest. This invention is based on design and construction of biosensors, composed of transcription factors and their cognate promoters, capable of binding an intracellular small molecule of interest. The presence of the small molecule of interest causes the transcription factor to modulate expression of the cognate promoter. The output of the promoter provides a means for screening or selecting for microorganisms producing the small molecule of interest. In specific, this invention involves a $\sigma^{54}$-dependent transcription factor and its cognate promoters. This class of transcription factors has been shown to bind to a broad range of industrial and commercial small molecules of interest. The small molecule of interest is a $C_2$-$C_8$ alcohol or aldehyde.

The screen/selection can be used to evolve microorganisms capable of producing increased amounts of the small molecule. Accurate, high throughput detection of intracellular metabolites remains a difficult task in biotechnology. Currently, low throughput chromatography methods are the gold standard in metabolite detection. The present invention provides a high throughput means to screen host cells or microorganisms, improving throughput by several orders of magnitude. In some embodiments, implementation of the present invention as a selection allows for direct, dynamic evolution of strains without the need for selections.

The present invention provides for a system comprising a BmoR, a $\sigma^{54}$-RNA polymerase, and a pBMO promoter operatively linked to a reporter gene, wherein the pBMO promoter is capable of expression of the reporter gene with an activated for of the BmoR and the $\sigma^{54}$-RNA polymerase.

The present invention provides for a system comprising a first nucleic acid encoding a BmoR, and a second nucleic acid encoding a pBMO promoter operatively linked to a reporter gene, wherein the system is capable of expressing a $\sigma^{54}$-RNA polymerase and the pBMO promoter is capable of expression of the reporter gene.

In some embodiments, the system is an in vitro system wherein all of the necessary components for transcription of the reporter gene, including but not limited to any necessary cofactors and nucleotide triphosphates, are present in the system.

In some embodiments, the system is an in vivo system wherein all of the necessary components for transcription of the reporter gene are present within a host cell.

In some embodiments of the present invention, the first nucleic acid and the second nucleic acid are each independently on a vector or integrated into a chromosome. The vector can be an expression vector or a plasmid. In some embodiments of the present invention, the vector is capable of stable maintenance in a host cell.

In some embodiments of the present invention, the first nucleic acid and the second nucleic acid are on a vector, such as a plasmid.

The nucleic acid that encodes the peptides of interest, such as BmoR, sigma 54, pBMO promoter-linked reporter gene of the present invention. The recombinant nucleic acid can be a double-stranded or single-stranded DNA, or RNA. The recombinant nucleic acid can encode an open reading frame (ORF) of BmoR, sigma 54, pBMO promoter-linked reporter gene. The recombinant nucleic acid can also comprise promoter sequences for transcribing the ORF in a suitable host cell. The recombinant nucleic acid can also comprise sequences sufficient for having the recombinant nucleic acid stably replicate in the host cell. The recombinant nucleic acid can be replicon capable of stable maintenance in a host cell. In some embodiments, the replicon is a plasmid. The present invention also provides for a vector or expression vector comprising a recombinant nucleic acid of the present invention.

It will be apparent to one of skill in the art that a variety of recombinant vectors can be utilized in the practice of aspects of the invention. As used herein, "vector" refers to polynucleotide elements that are used to introduce recombinant nucleic acid into cells for either expression or replication. Selection and use of such vehicles is routine in the art. An "expression vector" includes vectors capable of expressing DNAs that are operatively linked with regulatory sequences, such as promoter regions. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in the host cells and those that remain episomal or those that integrate into the host cell genome.

The vectors may be chosen to contain control sequences operably linked to the resulting coding sequences in a manner that expression of the coding sequences may be effected in an appropriate host cell. Suitable control sequences include those that function in the host cells. If the cloning vectors employed to obtain encoded peptides of interest lack control sequences for expression operably linked to the encoding nucleotide sequences, the nucleotide sequences are inserted into appropriate expression vectors. This can be done individually, or using a pool of isolated encoding nucleotide sequences, which can be inserted into host vectors, the resulting vectors transformed or transfected into host cells, and the resulting cells plated out into individual colonies. Suitable control sequences for single cell cultures of various types of organisms are well known in the art. Control systems for expression in yeast are widely available and are routinely used. Control elements include promoters, optionally containing operator sequences, and other elements depending on the nature of the host, such as ribosome binding sites. Particularly useful promoters for prokaryotic host cells include those promoters that are native to the peptide of interest. However, other bacterial promoters, such as those derived from sugar metabolizing enzymes, such as galactose, lactose (lac) and maltose, are also useful. Additional examples include promoters derived from biosynthetic enzymes such as for tryptophan (trp), the β-lactamase (bla), bacteriophage lambda PL, and T5. In addition, synthetic promoters, such as the tac promoter (U.S. Pat. No. 4,551,433; hereby incorporated by reference), can be used.

Selectable markers can also be included in the recombinant expression vectors with the proviso that the selectable markers are not the reporter gene. A variety of markers are known which are useful in selecting for transformed cell lines and generally comprise a gene whose expression confers a selectable phenotype on transformed cells when the cells are grown in an appropriate selective medium. Such markers include, for example, genes that confer antibiotic resistance or sensitivity to the plasmid.

The nucleic acid sequences or nucleotide sequences described herein, or a mixture of such sequences, can be cloned into one or more recombinant vectors as individual cassettes, with separate control elements or under the control of a single promoter. Methods for introducing the recombinant vectors of the present invention into suitable hosts are known to those of skill in the art and typically include the use of $CaCl_2$ or other agents, such as divalent cations, lipofection, DMSO, protoplast transformation, conjugation, and electroporation.

Sigma 54 ($\sigma^{54}$)

The system comprises a $\sigma^{54}$ or has the capability of expressing $\sigma^{54}$. Any $\sigma^{54}$ can be used that can be used to initiate transcription from the pBMO promoter.

A suitable $\sigma^{54}$ is the $\sigma^{54}$ of *Pseudomonas putida*. The amino acid sequence of the $\sigma^{54}$ of *Pseudomonas putida* comprises:

```
                                                      (SEQ ID NO: 1)
  1 mkpslvlkmg qqltmtpqlq qairllqlst ldlqqeiqea lesnpmlerq edgedfdnsd 61 pmadnaenkp aaevqdnsfq estvsadnle dgewseripn elpvdtawed iyqtsasslp 121 sndddewdft trtsageslq shllwqlnla pmsdtdrlia vtlidsingq gyledtleei 181 sagfdpeldi eldeveavlh riqqfepagv garnlgecll lqlrqlpatt pwmteakrlv 241 tdfidllgsr dysqlmrrmk ikedelrqvi elvqslnprp gsqiessepe yvvpdvivrk 301 dsdrwlveln qeaiprlrvn pqyagfvrra dtsadntfmr nqlqearwfi kslqsrnetl 361 mkvatriveh qrgfldhgde amkplvlhdi aeavgmhest isrvttqkym htprgiyelk 421 yffsshvsts eggecsstai raiikklvaa enqkkplsds kiaglleaqg iqvarrtvak 481 yreslgiaps serkrlm
```

A suitable σ⁵⁴ is the σ⁵⁴ of *Pseudomonas aerogenosa*. The amino acid sequence of the σ⁵⁴ of *Pseudomonas aerogenosa* comprises:

```
                                                      (SEQ ID NO: 2)
  1 mkpslvlkmg qqltmtpqlq qairllqlst ldlqqeiqea lesnpmlerq edgddfdnsd 61 pladgaeqaa sapqesplqe satpsvesld ddqwseripe elpvdtawed iyqtsasslp 121 sndddewdft artssgeslh shllwqvnla pmsdtdrmia vtiidsinnd gyleesleei 181 laaidpeldv eldevevvlr riqqlepagi garnlrecll lqlrqlpstt pwlnealrlv 241 sdyldllggr dysqlmrrmk lkedelrqvi eliqclhprp gsqiesseae yivpdvivrk 301 dnerwlveln qeamprlrvn atyagmvrra dssadntfmr nqlqearwfi ktlqsrnetl 361 mkvatqiveh qrgfldygee amkplvlhdi aeavgmhest isrvttqkym htprgifelk 421 yffsshvsta eggecsstai raiikklvaa enakkplsds kiaglleaqg iqvarrtvak 481 yreslgiaps serkrlv
```

A suitable σ⁵⁴ is the σ⁵⁴ of *Vibrio fischeri* ES 114. The amino acid sequence of the σ⁵⁴ of *Vibrio fischeri* ES114 comprises:

```
                                                      (SEQ ID NO: 3)
  1 mkaslqlkmg qqlamtpqlq qairllqlst ldlqqeiqea ldsnplldve eealstpetl 61 tspepkseke tasaeqetpi tdssdviesn niseelemda swddvysans gstglaiddd 121 tpiyqggette slqdylmwqa dltpftdldr tiattiiesl deygyltssl ddilesigde 181 evemdeveav lkriqqfdpl gvasrdlaec lllqlatypa ntpwlpetkl ilkdhinllg 241 nrdyrqlake tklkesdlkq vmmliheldp rpgnrvidte teyvipdvsv fkhngkwvvt 301 inpdsvprlk vnaeyaalgk tmgntpdgqf irtnlqeakw likslesrne tllkvarciv 361 ehqqdffeyg eeamkpmvin dialdvdmhe stisrvttqk fmhtprgife lkyffsshvs 421 tdnggecsst airalvkklv aaenqakpls dskiatllae qgiqvarrti akyreslgia 481 psnqrkrll
```

A suitable σ⁵⁴ is the σ⁵⁴ of *Escherichia coli* K12. The amino acid sequence of the σ⁵⁴ of *Escherichia coli* K12 comprises:

```
                                                      (SEQ ID NO: 17)
  1 mkqglqlrls qqlamtpqlq qairllqlst lelqqelqqa lesnplleqi dtheeidtre 61 tqdsetldta daleqkempe elpldaswdt iytagtpsgt sgdyiddelp vyqgettqtl
```

```
121 qdylmwqvel tpfsdtdrai atsivdavde tgyltvpled ilesigdeei dideveavlk 181 riqrfdpvgv aakdlrdcll iqlsqfdktt pwleearlii sdhldllanh dfrtlmrvtr 241 lkedvlkeav nliqsldprp gqsiqtgepe yvipdvlvrk hnghwtveln sdsiprlqin 301 qhyasmcnna rndgdsqfir snlqdakwli kslesrndtl lrvsrciveq qqaffeqgee 361 ymkpmvladi aqavemhest isrvttqkyl hsprgifelk yffsshvnte gggeasstai 421 ralvkkliaa enpakplsds kltsllseqg imvarrtvak yreslsipps nqrkqlv
```

The amino acid sequence from the E. coli $\sigma^{54}$ RNA polymerase (RpoN) and Pseudomonas putida (the most closely related organism to Pseudomonas butanovora for which a sequence is available) have about 52% sequence identity (with 70% positive matches), and the activator interacting domains exhibit 86% sequence identity. The E. coli $\sigma^{54}$-RNA polymerase is shown to be capable of initiating transcription of pBMO (see Example 1).

The system or host cell of the present invention can comprise a nucleic acid encoding any of the suitable $\sigma^{54}$. In some embodiments of the invention, a nucleic acid encoding any of the suitable $\sigma^{54}$ comprises the rpoN gene and is capable of expression in the present invention. The nucleic acid encoding any of the suitable $\sigma^{54}$ or the rpoN gene is operatively linked any promoter which is capable of expression in the system or host cell. In some embodiments, the promoter operatively linked to the suitable $\sigma^{54}$ or the rpoN gene is constitutively expressed, or is the native promoter of the rpoN gene.

BmoR

The BmoR becomes activated upon contact with a $C_2$-$C_8$ alcohol. BmoR in the active form together with the $\sigma^{54}$-RNA polymerase initiates transcription from the pBMO promoter.

The amino acid sequence of BmoR comprises:

```
                                                              (SEQ ID NO: 4)
  1 mskmqefarl etvasmrrav wdgnecqpgk vadvvlrswt rcraegvvpn arqefdpipr 61 taldetveak ralilaaepv vdalmeqmnd aprmiilnde rgvvllnqgn dtlledarrr 121 avrvgvcwde hargtnamgt alaerrpvai hgaehylesn tiftctaapi ydpfgeftgi 181 ldisgyagdm gpvpipfvqm avqfienqlf rqtfadcill hfhvrpdfvg tmregiavls 241 regtivsmnr aglkiaglnl eavadhrfds vfdlnfgafl dhvrqsafgl vrvslyggvq 301 vyarvepglr vpprpaahar pprpaprpld sldtgdaavr laidrarrai grnlsiliqg 361 etgagkevfa khlhaesprs kgpfvavnca aipegliese lfgyeegaft ggrrkgnigk 421 vaqahggtlf ldeigdmapg lqtrllrvlq dravmplggr epmpvdialv cathrnlrsl 481 iaqgqfredl yyrlnglais lpplrqrsdl aalvnhilfq ccggephysv spevmtlfkr 541 hawpgnlrql hnvldaalam lddghvieph hlpedfvmev dsglrpieed gstaahrarq 601 pasgsgpakk lqdlaldaie qaieqnegni svaarqlgvs rttiyrklrq lsptgchrpa 661 hwsqsrigt
```

The system or host cell of the present invention can comprise a nucleic acid encoding any of the BmoR. In some embodiments of the invention, a nucleic acid encoding the BmoR comprises the P. butanovora bmoR gene and is capable of expression in the present invention. The nucleic acid encoding the BmoR or the bmoR gene is operatively linked any promoter which is capable of expression in the system or host cell. In some embodiments, the promoter operatively linked to the BmoR or the bomR gene is constitutively expressed, or is the native promoter of the bmoR gene.

A BmoR in the active form is capable of binding DNA and facilitating the binding of a $\sigma^{54}$-RNA polymerase with a $\sigma^{54}$-specific promoter. BmoR comprises an activator-interaction domain, an ATPase domain, and a C-terminal helix-turn-helix DNA-binding domain.

BmoR is capable of sensing a $C_2$-$C_8$ alcohol or aldehyde. When BmoR senses a $C_2$-$C_8$ alcohol or aldehyde, it converts into the active form. The $C_2$-$C_8$ alcohol can be any $C_2$ alcohol, any $C_3$ alcohol, any $C_4$ alcohol, any $C_5$ alcohol, any $C_6$ alcohol, any $C_7$ alcohol, any $C_8$ alcohol, or a mixture thereof. In some embodiments of the invention, the $C_2$-$C_8$ alcohol is a $C_2$-$C_5$ alcohol, which can be any $C_2$ alcohol, any $C_3$ alcohol, any $C_4$ alcohol, any $C_5$ alcohol, or a mixture thereof. In some embodiments of the invention, the $C_2$-$C_5$ alcohol is a primary alcohol. In some embodiments of the invention, the $C_2$ alcohol is ethanol. In some embodiments, the $C_2$-$C_8$ alcohol includes alcohols of one, two, or three hydroxyl groups. In some embodiments of the invention, the $C_3$ alcohol is propan-1-ol or propan-2-ol. In some embodiments of the invention, the $C_4$ alcohol is butan-1-ol (n-butanol) or 2-methylpropan-1-ol (isobutanol). The $C_2$-$C_8$ aldehyde can be any $C_2$ aldehyde, any $C_3$ aldehyde, any $C_4$ aldehyde, any $C_5$ aldehyde, any $C_6$ aldehyde, any $C_7$ aldehyde, any $C_8$ aldehyde, or a mixture thereof.

BmoR has been shown to be capable of activating pBMO-promoter expression in E. coli in response to butan-1-ol, 1-propanol, 2-propanol, 1-pentanol, 1-hexanol, and ethanol.

The pBMO Promoter

The pBMO promoter comprises the nucleotide sequence of a $\sigma^{54}$-dependent promoter. The pBMO promoter is any nucleic acid sequence that is capable of initiation of transcription in the presence of a $\sigma^{54}$-RNA polymerase and a BmoR in the active form.

In some embodiments of the invention, the $\sigma^{54}$-dependent promoter comprises the following nucleotide sequence: MRNNN TGGCACRN $N_3$ TTGCW NN (SEQ ID NO:5) or MRNNN TGGCACRN $N_4$ TTGCW NN (SEQ ID NO:6), wherein M is C or A; R is A or G; W is A or T; and N is A, G, C or T. In some embodiments of the invention, the $\sigma^{54}$-dependent promoter comprises the following nucleotide sequence: MRNRY TGGCACGN $N_3$ TTGCW NN (SEQ ID NO:7) or MRNRY TGGCACGN $N_4$ TTGCW NN (SEQ ID NO:8), wherein M is C or A; R is A or G; Y is C or T; W is A or T; and N is A, G, C or T. In some embodiments of the invention, the $\sigma^{54}$-dependent promoter comprises the following nucleotide sequence: AANNN TGGCACAG NNNN TTGCA TATT (SEQ ID NO:9), wherein N is A, G, C or T. In some embodiments of the invention, the $\sigma^{54}$-dependent promoter comprises the following nucleotide sequence: CATGC TGGCACGA CAC TTGCT GAA (SEQ ID NO:10).

In some embodiments of the invention, the pBMO promoter comprises the following nucleotide sequence:

```
                                           (SEQ ID NO: 11)
ccacagatag taggtgctgc ggctgctcat gctcctgtcg cggtagcgcg ctgttacgcg accgcccccg gacctcggcg gacagcgcgg aagattggaa acagcccgag cgtgcgtgcc tcgggctgca tccttgccac acccaaccgg attcgtcgga ccgctcgaca ttcgcgttcg ctcccgcggc gccgcgggtg taccgttgcg ttacagatgt acccttcttt aacgtgtaac acacgcctgg agcggccaag agcccccgcac cttgcggcgc gtcttcccca ggggcccacc ggttgcggcc ttttgctgcg accgtc (MRNNN TGGCACRN N3 TTGCW NN)

aagcgttaga g
or
                                           (SEQ ID NO: 12)
ccacagatag taggtgctgc ggctgctcat gctcctgtcg cggtagcgcg ctgttacgcg accgcccccg gacctcggcg gacagcgcgg aagattggaa acagcccgag cgtgcgtgcc tcgggctgca tccttgccac acccaaccgg attcgtcgga ccgctcgaca ttcgcgttcg ctcccgcggc gccgcgggtg taccgttgcg ttacagatgt acccttcttt aacgtgtaac acacgcctgg agcggccaag agcccccgcac cttgcggcgc gtcttcccca ggggcccacc ggttgcggcc ttttgctgcg accgtc (MRNNN TGGCACRN N4 TTGCW NN)

aagcgttaga g
``` wherein M is C or A; R is A or G; W is A or T; and N is A, G, C or T, and the next nucleotide on the 3' end marks the approximate +1 transcription start site of transcription of the pBMO promoter.

In some embodiments of the invention, the pBMO promoter comprises the following nucleotide sequence:

```
                                           (SEQ ID NO: 13)
ccacagatag taggtgctgc ggctgctcat gctcctgtcg cggtagcgcg ctgttacgcg accgcccccg gacctcggcg gacagcgcgg aagattggaa acagcccgag cgtgcgtgcc tcgggctgca tccttgccac acccaaccgg attcgtcgga ccgctcgaca ttcgcgttcg ctcccgcggc gccgcgggtg taccgttgcg ttacagatgt acccttcttt aacgtgtaac acacgcctgg agcggccaag agcccccgcac cttgcggcgc gtcttcccca ggggcccacc ggttgcggcc ttttgctgcg accgtc (MRNRY TGGCACGN N3 TTGCW NN)

aagcgttaga g
or
                                           (SEQ ID NO: 14)
ccacagatag taggtgctgc ggctgctcat gctcctgtcg cggtagcgcg ctgttacgcg accgcccccg gacctcggcg gacagcgcgg aagattggaa acagcccgag cgtgcgtgcc tcgggctgca tccttgccac acccaaccgg attcgtcgga ccgctcgaca ttcgcgttcg ctcccgcggc gccgcgggtg taccgttgcg ttacagatgt acccttcttt aacgtgtaac acacgcctgg agcggccaag agcccccgcac cttgcggcgc gtcttcccca ggggcccacc ggttgcggcc ttttgctgcg accgtc (MRNRY TGGCACGN N4 TTGCW NN)

aagcgttaga g
``` wherein M is C or A; R is A or G; W is A or T; and N is A, G, C or T, and the next nucleotide on the 3' end marks the approximate +1 transcription start site of transcription of the pBMO promoter.

In some embodiments of the invention, the pBMO promoter comprises the following nucleotide sequence:

```
                                           (SEQ ID NO: 15)
ccacagatag taggtgctgc ggctgctcat gctcctgtcg cggtagcgcg ctgttacgcg accgcccccg gacctcggcg gacagcgcgg aagattggaa acagcccgag cgtgcgtgcc tcgggctgca tccttgccac acccaaccgg attcgtcgga ccgctcgaca ttcgcgttcg ctcccgcggc gccgcgggtg taccgttgcg ttacagatgt acccttcttt aacgtgtaac acacgcctgg agcggccaag agcccccgcac cttgcggcgc gtcttcccca ggggcccacc ggttgcggcc ttttgctgcg accgtc (AANNN TGGCACAG NNNN TTGCA TATT)

aagcgttaga g
``` wherein N is A, G, C or T, and the next nucleotide on the 3' end marks the approximate +1 transcription start site of transcription of the pBMO promoter.

In some embodiments of the invention, the pBMO promoter comprises the following nucleotide sequence:

```
                                                    (SEQ ID NO: 16)
ccacagatag taggtgctgc ggctgctcat gctcctgtcg cggtagcgcg ctgttacgcg accgcccccg gacctcggcg gacagcgcgg aagattggaa acagcccgag cgtgcgtgcc tcgggctgca tccttgccac acccaaccgg attcgtcgga ccgctcgaca ttcgcgttcg ctcccgcggc gccgcgggtg taccgttgcg ttacagatgt acccttcttt aacgtgtaac acacgcctgg agcggccaag agccccgcac cttgcggcgc gtcttcccca ggggcccacc ggttgcggcc ttttgctgcg accgtccatg ctggcacgac acttgctgaa agcgttagag
``` wherein the next nucleotide on the 3' end marks the approximate +1 transcription start site of transcription of the pBMO promoter. The promoter is underlined.

The Host Cell

The present invention provides for a modified host cell comprising a first nucleic acid encoding a BmoR, and a second nucleic acid encoding a pBMO promoter operatively linked to a reporter gene, wherein the modified host cell is capable of expressing a $\sigma^{54}$-RNA polymerase.

In some embodiments of the invention, the host cell is a bacterium. In some embodiments of the invention, the bacterium is a Gram-negative β-proteobacterium. In some embodiments of the invention, the bacterium is any bacterium that expresses a $\sigma^{54}$. The $\sigma^{54}$ can be native or heterologous to the bacterium. In some embodiments of the invention, the bacterium is an enteric bacterium. In some embodiments of the invention, the bacterium has a native $\sigma^{54}$. In some embodiments of the invention, the bacterium is of the genus *Bacillus*, *Planctomyces*, *Bradyrhizobium*, *Rhodobacter*, *Rhizobium*, *Myxococcus*, *Klebsiella*, *Azotobacter*, *Escherichia*, *Salmonella*, *Pseudomonas*, *Caulobacter*, *Chlamydia*, *Acinetobacter*, *Sinorhizobium*, *Enterococcus*, *Clostridium*, and *Vibrio*. In some embodiments of the invention, the $\sigma^{54}$ is native to the host cell. In some embodiments of the invention, the $\sigma^{54}$ is heterologous to the host cell, wherein the host cell optionally does not express its native $\sigma^{54}$. In some embodiments of the invention, the bacterium is *E. coli*.

One embodiment of the present invention is an in vivo biosensor in *E. coli* for the detection of a $C_2$-$C_8$ alcohol or aldehyde, including but not limited to ethanol to octanol. Such a biosensor has applications in the development of high-throughput selections and screens for use in engineering microorganisms producing alcohol-based biofuel molecules. Included in the applications would be protein, operon, genome, transporter, and organism-level engineering approaches. Selections are the gold-standard in engineering applications because they provide several orders-of-magnitude increased throughput compared to screens; thereby, a user is enabled to test more conditions, faster. The present invention is highly valuable in engineering organisms for biofuels production.

Methods of the Present Invention

The present invention provides for a method for sensing a $C_2$-$C_8$ alcohol or aldehyde, comprising: (a) providing a modified host cell of the present invention, and (b) detecting the expression of the reporter gene. The $C_2$-$C_8$ alcohol can be any $C_2$ alcohol, any $C_3$ alcohol, any $C_4$ alcohol, any $C_5$ alcohol, any $C_6$ alcohol, any $C_7$ alcohol, any $C_8$ alcohol, or a mixture thereof. In some embodiments of the invention, the $C_2$-$C_8$ alcohol is a $C_2$-$C_5$ alcohol, which can be any $C_2$ alcohol, any $C_3$ alcohol, any $C_4$ alcohol, any $C_5$ alcohol, or a mixture thereof. In some embodiments of the invention, the $C_2$-$C_5$ alcohol is a primary alcohol. In some embodiments of the invention, the $C_2$ alcohol is ethanol. In some embodiments, the $C_2$-$C_8$ alcohol includes alcohols of one, two, or three hydroxyl groups. In some embodiments of the invention, the $C_3$ alcohol is propan-1-ol or propan-2-ol. In some embodiments, the alcohol is butan-1-ol, 1-propanol, 2-propanol, 1-pentanol, 1-hexanol, ethanol, or a mixture thereof. In some embodiments of the invention, the $C_4$ alcohol is butan-1-ol (n-butanol) or 2-methylpropan-1-ol (isobutanol). The $C_2$-$C_8$ aldehyde can be any $C_2$ aldehyde, any $C_3$ aldehyde, any $C_4$ aldehyde, any $C_5$ aldehyde, any $C_6$ aldehyde, any $C_7$ aldehyde, any $C_8$ aldehyde, or a mixture thereof.

In some embodiments of the invention, the (b) detecting step comprises detecting the gene product of the reporter gene. In some embodiments of the invention, the gene product of the reporter gene increases or decreases the doubling time of the modified host cell. In some embodiments of the invention, the gene product of the reporter gene causes the modified host cell to become resistant or sensitive to a compound.

The present invention provides for a method for screening or selecting a host cell that produces a $C_2$-$C_8$ alcohol or aldehyde, comprising: (a) providing a modified host cell of the present invention, (b) culturing the host cell, and (c) screening or selecting the host cell based the expression of the reporter gene by the host cell.

In some embodiments of the present invention, the method for screening or selecting a host cell that produces a $C_2$-$C_8$ alcohol or aldehyde, comprises: (a) providing a plurality of modified host cells of the present invention wherein the modified host cells of different modification are in separate cultures, (b) culturing each separate culture of host cell, (c) screening or selecting the host cell based the expression of the reporter gene by the host cell, and (d) comparing the expression of the reporter genes of the separate cultures. In some embodiments of the present invention, the (d) comprising step comprises identifying one or more cultures, and/or the corresponding host cell, that have an increased expression of the gene product of the reporter gene.

In some embodiments, the method is a method for selecting a host cell that produces a $C_2$-$C_8$ alcohol or aldehyde, wherein the selection is a positive selection or a negative selection. When the selection is positive selection, the selecting step selects for host cells that have a higher expression of a reporter gene that increases the probability of remaining viable and doubling, and thus have a higher probability of remaining viable and doubling. When the selection is negative selection, the selecting step selects for host cells that have a lower expression of the reporter gene that decreases the probability of remaining viable and doubling, and thus have a higher probability of remaining viable and doubling.

In one embodiment of the present invention, the method for selecting an *E. coli* host cell that produces a $C_2$-$C_8$ alcohol or aldehyde comprises: (a) providing a plurality of modified *E. coli* host cells of the present invention wherein the modified host cells of different modification are in separate cultures, (b) culturing each separate culture of host cell, (c) selecting the host cell based the expression of the reporter gene by the host cell, and (d) comparing the expression of the reporter genes of the separate cultures, wherein the selecting is a positive selecting.

In another embodiments of the present invention, the method for selecting an *E. coli* host cell that produces a $C_2$-$C_8$ alcohol or aldehyde comprises: (a) providing a plurality of modified *E. coli* host cells of the present invention wherein the modified host cells of different modification are in separate cultures, (b) culturing each separate culture of host cell, (c) selecting the host cell based the expression of the reporter gene by the host cell, and (d) comparing the expression of the reporter genes of the separate cultures, wherein the selecting is a negative selecting.

In some embodiments of the invention, the compound is an antibiotic and the reporter gene is an antibiotic resistance gene which confers resistance to the antibiotic. In some embodiments of the invention, the reporter gene is cat or bla. The reporter gene can be used as a positive selection or as a negative selection. Positive selection occurs when the increased expression of the gene product of the reporter gene increases the probability that the host cell would remain viable and complete doubling. Examples of reporter genes that confer positive selection are antibiotic resistance genes that confer resistance to an antibiotic of the host cell when the host cell is cultured or grown in a culture containing the antibiotic. An example of such as is a β-lactamase, encoded by the bla gene. Other examples of reporter genes that confer positive selection are genes encoding enzymes that are required by the host cell to metabolize a specific nutrient source which is required by the host cell in order to remain viable and double. Negative selection occurs when the increased expression of the gene product of the reporter gene decreases the probability that the host cell would remain viable and complete doubling. Examples of reporter genes that confer negative selection are genes which when expressed inhibit resistance to an antibiotic of the host cell when the host cell is cultured or grown in a culture containing the antibiotic. An example of such as inhibitor is a β-lactamase inhibitor, such as clavulanic acid, which inhibits a β-lactamase, such as ampicillin.

A putative $\sigma^{54}$-governed promoter (pBMO) was first described in the n-alkane metabolizing microbe *Pseudomonas butanovora* (Sluis, M. K., Sayavedra-Soto, L. A. & Arp, D. J. Molecular analysis of the soluble butane monooxygenase from '*Pseudomonas butanovora*'. *Microbiology* 148, 3617-3629 (2002), which is incorporated by reference). More recently, Kurth et al. described an activator protein (BmoR) for pBMO that is responsive to short-chain ($C_2$-$C_8$) alcohols (Kurth, E. G., Doughty, D. M., Bottomley, P. J., Arp, D. J. & Sayavedra-Soto, L. A. Involvement of BmoR and BmoG in n-alkane metabolism in '*Pseudomonas butanovora*'. *Microbiology* 154, 139-147 (2008), which is incorporated by reference). Insertion of LacZ downstream of pBMO on the genome was employed for characterization of promoter efficiency in response to various alcohols and to measure leaky expression (BmoR knockout) (see FIG. 1).

When grown on lactate, leaky expression was found to be negligible, and the activator protein was found to respond to even alcohols of varying chain length. Induction of BMO in following carbon limitation in the absence of BmoR is an indication that there is at least one additional mechanism of regulating pBMO.

The invention having been described, the following examples are offered to illustrate the subject invention by way of illustration, not by way of limitation.

EXAMPLE 1

Characterization of the pBMO Promoter

Construction of an *E. Coli* Strain Containing a pBMO-promoter::GFP Reporter Cassette.

Figure 3:
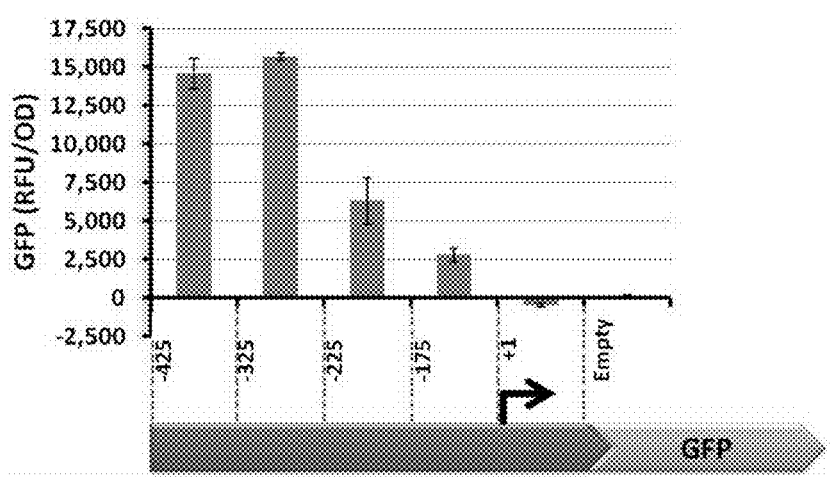
FIG. 3 shows the transcriptional expression from various pBMO::GFP (green fluorescence protein) constructs which vary in the length of upstream region of pBMO in response to butan-1-ol.

A pBMO-promoter::GFP reporter cassette is constructed. The pBMO-promoter comprises the nucleotide sequences from the −425 nucleotide to the +11 nucleotide. This section of the pBMO-promoter comprises the upstream activating sequence (UAS) to which BmoR binds. A deletion analysis is performed whereby the upstream sequence is deleted to produce reporter cassettes comprising of the −325 nucleotide to the +1 nucleotide fragment, the −225 nucleotide to the +1 nucleotide fragment, the −175 nucleotide to the +1 nucleotide fragment, the +1 nucleotide to the +1 nucleotide fragment, and no fragment (FIG. 3). The various reporter cassettes are introduced into an *E. coli.* also containing the bmoR gene operatively linked to the pBAD promoter or a pZT promoter. The pBAD promoter is taught by Guzman, L. M., et al., "Tight regulation, modulation, and high-level expression by vectors containing the arabinose PBAD promoter", *J. Bacteriol.* 177(14):4121-4130 (1995), which is incorporated by reference. The pZT promoter is taught by Skerra, A, "Use of the tetracycline promoter for the tightly regulated production of a murine antibody fragment in *Escherichia coli*", *Gene* 151:131-135 (1994), which is incorporated by reference. Measuring the GFP activity of each strain indicates that the nucleotide sequence from the −325 to −225 nucleotides comprises nucleotide sequence that is essential is BmoR mediated gene activation (FIG. 3).

Determination of the Optimum Temperature for butan-1-ol Activation of the pBMO-promoter::GFP Reporter Cassette.

Figure 4:
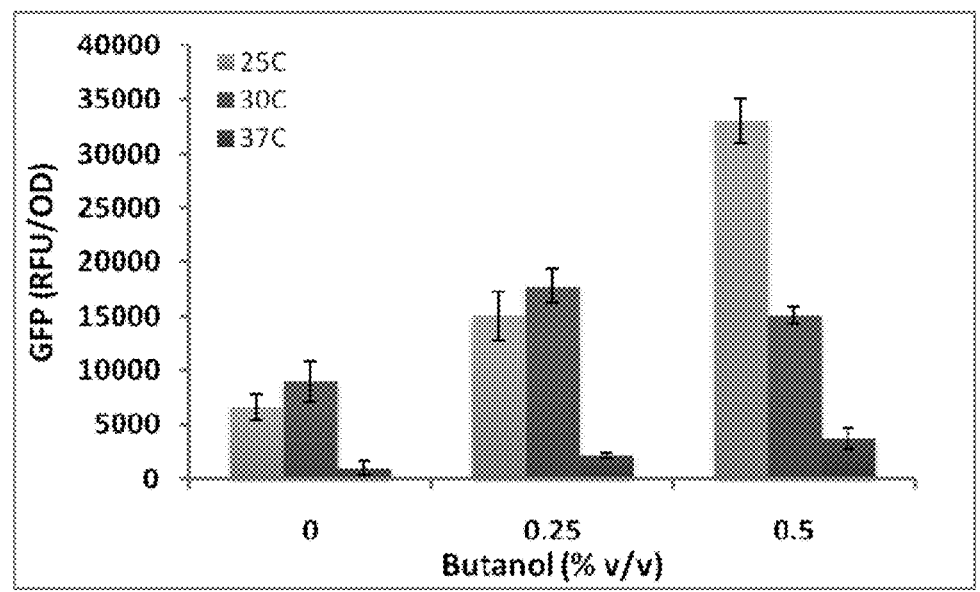
FIG. 4 shows the transcriptional expression from a pBMO::GFP construct when host cells are cultured in different concentrations of butan-1-ol and different temperatures.

Using the pBMO-promoter reporter cassette comprising of the −325 nucleotide to the +1 nucleotide fragment, the *E. coli* strain is analyzed for the optimum temperature for pBMO promoter activity using different concentrations of butan-1-ol. Compared to the other conditions tested, when the strain is cultured at 25° C. with 0.5% of butan-1-ol by volume, the activation of the reporter gene is the strongest (FIG. 4).

Activation of the pBMO-promoter::GFP Reporter Cassette in Response to Various Alcohols.

Figure 5:
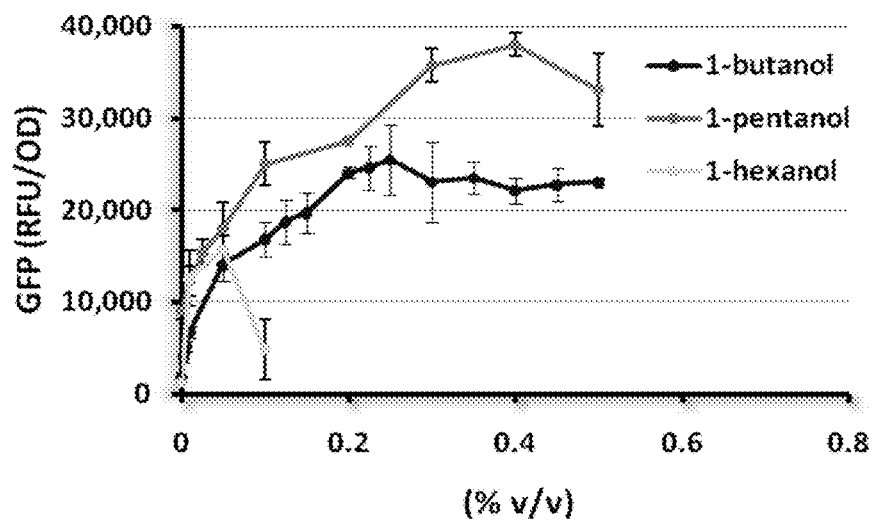
FIG. 5 shows the transcriptional expression from a pBMO::GFP construct in response to varying amounts of butan-1-ol, 1-pentanol, and 1-hexanol.
Figure 6:
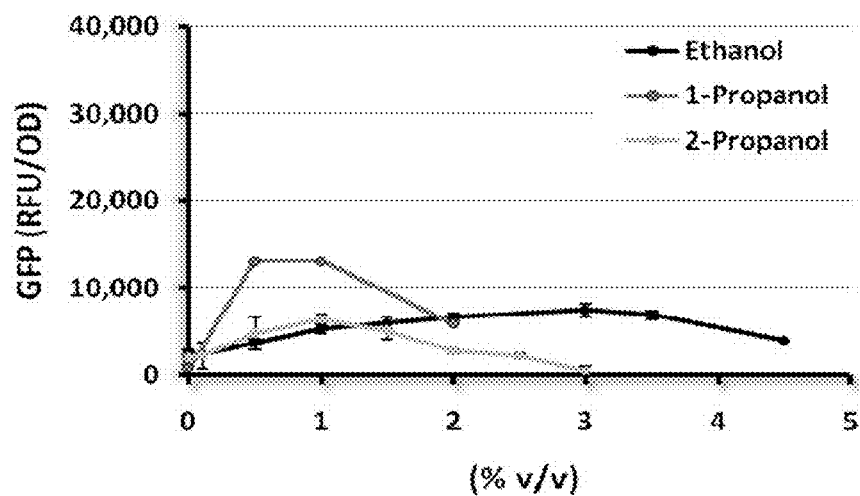
FIG. 6 shows the transcriptional expression from a pBMO::GFP construct in response to varying amounts of ethanol, 1-propanol, and 2-propanol.

Using the pBMO-promoter reporter cassette comprising of the −325 nucleotide to the +1 nucleotide fragment, the *E. coli* strain is analyzed for pBMO promoter activity in response to different alcohols: butan-1-ol (FIG. 5), ethanol (FIG. 6), 1-propanol (FIG. 6), 2-propanol (FIG. 6), pentanol (FIG. 5), and hexanol (FIG. 5). From an overnight culture harboring a plasmid containing GFP under control of pBMO and BmoR under control of pZT 5 mL cultures of rich media were inoculated (1.5% v/v). Cultures are grown at 37° C., 200 rpm, until reaching an optical density ($OD_{600}$) of 0.25 and induced with 57.5 ng/mL anhydrotetracyline. The cultures are than grown at 25° C., 200 rpm, until reaching an $OD_{600}$=0.80 at which point they are diluted to an $OD_{600}$=0.20 in media containing a range of alcohol concentrations. The culture tubes are sealed with parafilm and grown at 25° C., 200 rpm, for 18 hours. 150 μl culture samples are quantified for GFP fluorescence on a 96-well plate reader.

Purification of BmoR.

Figure 7:
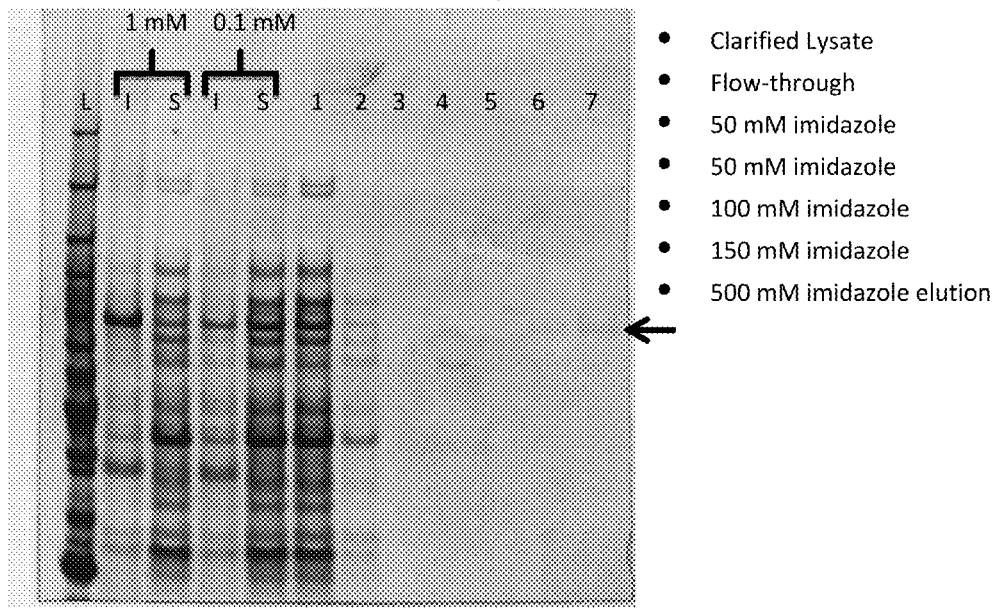
FIG. 7 shows the isolation of His-tagged BmoR. The arrow indicates the band corresponding to isolated BmoR.

The BmoR gene is linked to a His-tag in a His-tag purification system, such as from Qiagen Inc.—USA (Valencia, Calif.) or Novagen® (Madison, Wis.). 500 mL cultures of *E. coli* harboring a His-tagged version of BmoR under control of a pBAD promoter were grown in terrific broth (TB) media for 12 hours with inducing concentrations of arabinose (0.5 mM) at 25° C. The cultures are centrifuged (8000×g, 4° C., 5 min) and resuspended in 10 mL of 50 mM Tris (pH 8.0), 50 mM KCl buffer. Following, the cells are lysed by sonication, and recentrifuged (10,000×g, 4° C., 10 min) and passed through a 0.45 μm filter. The BmoR protein is then purified using a Ni-NTA agarose slurry according to the manufacturer's protocol (Qiagen Inc, Valencia, Calif. USA). BmoR is purified at the final 500 mM imidazole elution step to a purity of over 99% (FIG. 7).

Gel Mobility Shift Assay.

Figure 8:
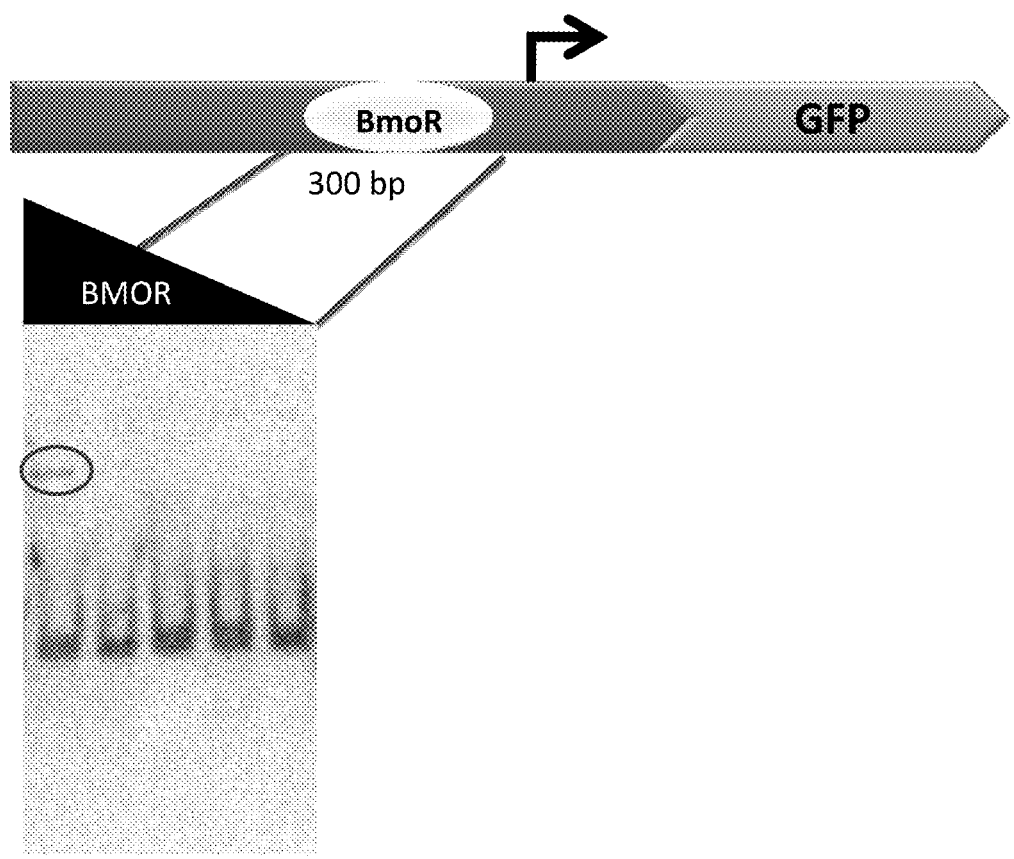
FIG. 8 shows the characterization of the BmoR DNA-binding site on the pBMO promoter. The oval on the gel indicates the shifted band indicating the binding of BmoR.

Purified protein is also used to demonstrate BmoR binding to a 300-nucleotide DNA fragment upstream of the pBMO-promoter. A DIG Gel Shift Kit (Roche Applied Science, Indianapolis, Ind.) is used according to the manufacturer's instructions. A band shift is observed when a gel mobility shift assay is performed indicating binding of the BmoR transcription factor upstream of the pBMO-promoter (FIG. 8).

EXAMPLE 2 pBMO Biosensor

A functional in vivo biosensor for butanol and other short-chain alcohols has several applications. The impact of genome, protein, and pathways modifications made to vary in vivo butanol concentrations could be rapidly assessed. Positive and negative screening plasmids (FIG. 1) can be readily constructed, providing a fluorescence output signal ideally proportional to in vivo alcohol concentration. If a low level of basal expression can be achieved, strong selections can developed with an unrivaled ability for strain evolution.

First, BmoR can be engineered to be selective toward individual alcohols (rather than a wide range) to enable discrimination between fermentation products. Thus, the biosensor has applications in detecting concentrations of many in vivo products. Second, applying this system in protein, genome, and pathway engineering applications. A biosensor strain can be constructed by transformation of the host strain with a plasmid harboring the BmoR/pBMO system or by integrating the system onto the host microbe's genome. The reporter strain can be used to screen or select for individual microbes with improved production of an intracellular alcohol of interest. The alcohol or aldehyde can be produced either natively or through heterologous expression of a non-native pathway. Microbes with improved productivity can be subjected to directed evolution to further improve productivity yields for the target compound.

The BmoR transcription factor is used to construct a genetic selection for the presence of butanol in the media. By cloning in the gene encoding for the tetracycline antiporter TetA downstream of the $_p$BMO promoter E. coli is engineered to exhibit a growth dependent response to the presence of butanol.

Measure of E. coli Specific Growth Rates in the Presence of Butanol and Tetracycline.

Figure 9:
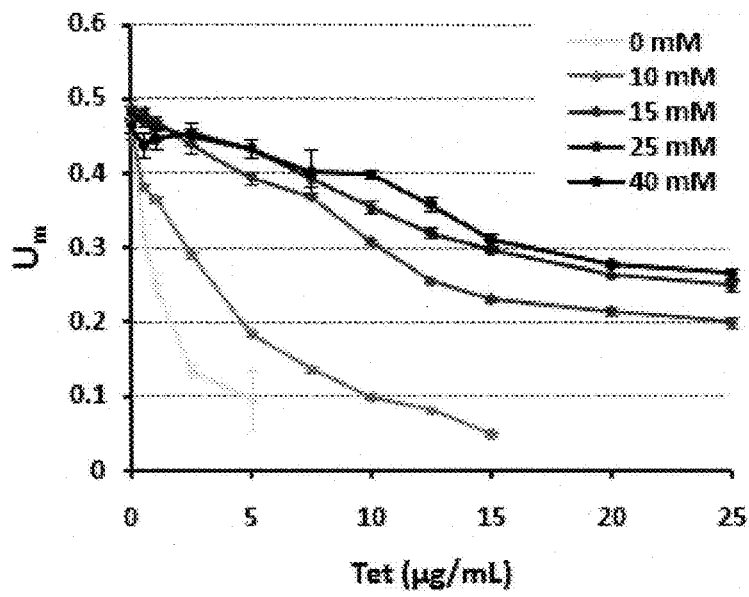
FIG. 9 shows the *E. coli* specific growth rates in varying concentrations of tetracycline and butanol. *E. coli* cultures harboring the butanol biosensor controlling TetA expression are inoculated into media containing multiple concentrations of butanol and tetracycline.

E. coli cultures harboring the butanol biosensor controlling TetA expression are inoculated into media containing multiple concentrations of butanol and tetracycline. Maximal growth rates are calculated by fitting curves to the Gompertz equation. E. coli exhibited strong butanol dependent growth up to concentrations at which butanol toxicity was measured. E. coli harboring an empty vector control exhibited growth only at 0 ug/mL tetracycline. N=4, mean±standard deviation. See FIG. 9.

Developing a High-Throughput Liquid Culture Screen for Butanol.

E. coli cultures harboring the butanol biosensor controlling TetA expression are exposed to a range of butanol and tetracycline concentrations and final cell densities are measured. User control over the time point post inoculation ($t_s$) at which tetracycline is applied, and the total culture period ($t_f$) enable a high degree of control over biosensor performance. At low $t_s$ and high $t_f$ a stringent selection for butanol can be achieved in the liquid culture media; increasing $t_s$ decreases assay stringency, but improves the linear range of detection. The results are used to produce "heat maps".

User-Defined Control Over Tetracycline $IC_{50}$.

Figure 10:
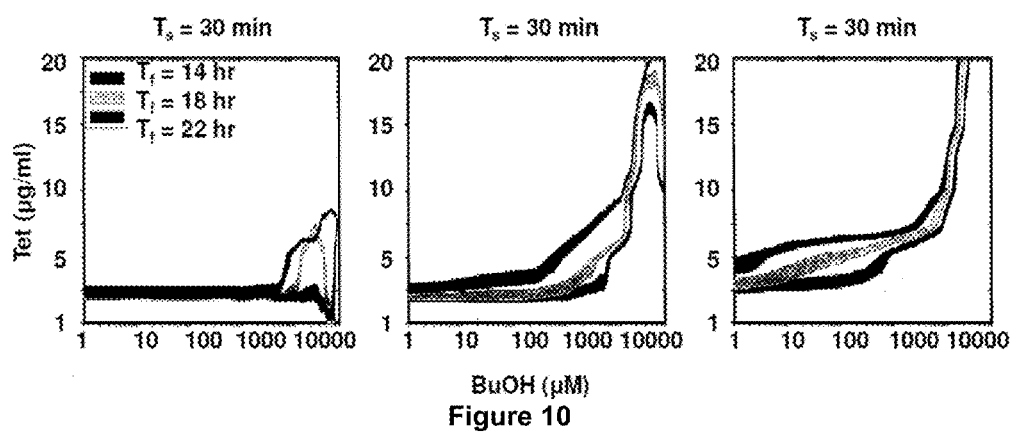
FIG. 10 shows the tetracycline concentration at which half maximal growth inhibition ($IC_{50}$) can be correlated to butanol concentration, $t_s$, and $t_f$.

From associated "heat maps", the tetracycline concentration at which half maximal growth inhibition ($IC_{50}$) can be correlated to butanol concentration, $t_s$, and $t_f$. By modulating these parameters, the biosensor can be tuned to select for different butanol concentrations in the media. See FIG. 10.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

---

What is claimed is:

1. An in vitro system comprising a BmoR transcription factor, a $\sigma^{54}$-RNA polymerase, and a pBMO promoter operatively linked to a reporter gene, wherein the pBMO promoter is capable of expression of the reporter gene with an activated form of the BmoR and the $\sigma^{54}$-RNA polymerase.

2. The system of claim 1 comprising (a) a first nucleic acid encoding the BmoR, and (b) a second nucleic acid, or optionally the first nucleic acid, encoding the pBMO promoter operatively linked to the reporter gene; wherein the system is capable of expressing the $\sigma^{54}$-RNA polymerase and the pBMO promoter is capable of expression of the reporter gene.

3. The system of claim 2, wherein the pBMO promoter comprises the nucleotide sequence depicted by one of SEQ ID NO:5-16.

4. The system of claim 1, wherein the BmoR is capable of sensing a $C_2$-$C_8$ alcohol.

5. The system of claim 4, wherein the BmoR is capable of sensing butan-1-ol, 1-propanol, 2-propanol, 1-pentanol, 1-hexanol, or ethanol.

6. A modified host cell comprising a first nucleic acid encoding a BmoR, and a second nucleic acid encoding a pBMO promoter operatively linked to a reporter gene, wherein the modified host cell is capable of expressing a $\sigma^{54}$-RNA polymerase, wherein the modified host cell is of the genus *Bacillus, Planctomyces, Bradyrhizobium, Rhodobacter, Rhizobium, Myxococcus, Klebsiella, Azotobacter, Escherichia, Salmonella, Caulobacter, Chlamydia, Acinetobacter, Sinorhizobium, Enterococcus, Clostridium*, or *Vibrio*.

7. The modified host cell of claim 6, wherein a gene product of the reporter gene increases or decreases the doubling time of the modified host cell in a particular environment.

8. The modified host cell of claim 6, wherein a gene product of the reporter gene causes the modified host cell to become resistant or sensitive to a compound.

9. The modified host cell of claim 6, wherein the BmoR is capable of sensing a $C_2$-$C_8$ alcohol.

10. The modified host cell of claim 9, wherein the BmoR is capable of sensing butan-1-ol, 1-propanol, 2-propanol, 1-pentanol, 1-hexanol, or ethanol.

11. The modified host cell of claim 6, wherein the pBMO promoter comprises the nucleotide sequence depicted by one of SEQ ID NO:5-16.

12. A method for sensing a C2-C8 alcohol, aldehyde, or mixture thereof, comprising: (a) providing a modified host cell comprises a first nucleic acid encoding a BmoR, and a second nucleic acid encoding a pBMO promoter operatively linked to a reporter gene, wherein the modified host cell is capable of expressing a $\sigma^{54}$-RNA polymerase and the pBMO promoter is capable of expression of the reporter gene, wherein the modified host cell is of the genus *Bacillus, Planctomyces, Bradyrhizobium, Rhodobacter, Rhizobium, Myxococcus, Klebsiella, Azotobacter, Escherichia, Salmonella, Caulobacter, Chlamydia, Acinetobacter, Sinorhizobium, Enterococcus, Clostridium*, or *Vibrio*, and (b) detecting the expression of the reporter gene.

13. The method of claim 12, wherein the (b) detecting step comprises detecting the gene product of the reporter gene.

14. The method of claim 13, wherein the gene product of the reporter gene increases or decreases the doubling time of the modified host cell.

15. The method of claim 13, wherein the gene product of the reporter gene causes the modified host cell to become resistant or sensitive to a compound.

16. The method of claim 12, wherein the BmoR is capable of sensing a $C_2$-$C_8$ alcohol.

17. The method of claim 16, wherein the BmoR is capable of sensing butan-1-ol, 1-propanol, 2-propanol, 1-pentanol, 1-hexanol, or ethanol.

18. The method of claim 12, wherein the pBMO promoter comprises the nucleotide sequence depicted by one of SEQ ID NO:5-16.

19. The modified host cell of claim 6, wherein the modified host cell is of the genus *Escherichia*.

20. The modified host cell of claim 19, wherein the modified host cell is *Escherichia coli*.

21. A modified host cell comprising a first nucleic acid encoding a BmoR, and a second nucleic acid encoding a pBMO promoter operatively linked to a reporter gene, wherein the modified host cell is capable of expressing a $\sigma^{54}$-RNA polymerase, wherein a gene product of the reporter gene increases or decreases the doubling time of the modified host cell in a particular environment, wherein the first nucleic acid or second nucleic acid is on a vector.

22. A modified host cell comprising a first nucleic acid encoding a BmoR, and a second nucleic acid encoding a pBMO promoter operatively linked to a reporter gene, wherein the modified host cell is capable of expressing a $\sigma^{54}$-RNA polymerase, wherein the first nucleic acid or second nucleic acid is on a vector.

23. The method of claim 12, wherein the modified host cell is of the genus *Escherichia*.

24. The method of claim 13, wherein the modified host cell is *Escherichia coli*.

25. The modified host cell of claim 21 or 22, wherein a gene product of the reporter gene increases or decreases the doubling time of the modified host cell in a particular environment.

26. The modified host cell of claim 21 or 22, wherein a gene product of the reporter gene causes the modified host cell to become resistant or sensitive to a compound.

27. The modified host cell of claim 21 or 22, wherein the BmoR is capable of sensing a $C^2$-$C^8$ alcohol.

28. The modified host cell of claim 27, wherein the BmoR is capable of sensing butan-1-ol, 1-propanol, 2-propanol, 1-pentanol, 1-hexanol, or ethanol.

29. The modified host cell of claim 21 or 22, wherein the pBMO promoter comprises the nucleotide sequence depicted by one of SEQ ID NO:5-16.

30. The modified host cell of claim 21 or 22, wherein the modified host cell is of the genus *Bacillus, Planctomyces, Bradyrhizobium, Rhodobacter, Rhizobium, Myxococcus, Klebsiella, Azotobacter, Escherichia, Salmonella, Caulobacter, Chlamydia, Acinetobacter, Sinorhizobium, Enterococcus, Clostridium*, or *Vibrio*.

31. The modified host cell of claim 20, wherein the modified host cell is of the genus *Escherichia*.

32. The modified host cell of claim 31, wherein the modified host cell is *Escherichia coli*.

* * * * *